United States Patent
Han et al.

(10) Patent No.: US 11,189,800 B2
(45) Date of Patent: Nov. 30, 2021

(54) HETEROCYCLIC COMPOUND AND ORGANIC LIGHT EMITTING DEVICE COMPRISING THE SAME

(71) Applicant: LG CHEM, LTD., Seoul (KR)

(72) Inventors: Mi Yeon Han, Daejeon (KR); Jung Oh Huh, Daejeon (KR); Boon Jae Jang, Daejeon (KR); Dong Hoon Lee, Daejeon (KR); Dong Uk Heo, Daejeon (KR)

(73) Assignee: LG CHEM, LTD., Seoul (KR)

( * ) Notice: Subject to any disclaimer, the term of this patent is extended or adjusted under 35 U.S.C. 154(b) by 428 days.

(21) Appl. No.: 16/331,498

(22) PCT Filed: Apr. 27, 2018

(86) PCT No.: PCT/KR2018/004954
§ 371 (c)(1),
(2) Date: Mar. 7, 2019

(87) PCT Pub. No.: WO2019/013437
PCT Pub. Date: Jan. 17, 2019

(65) Prior Publication Data
US 2019/0207120 A1 Jul. 4, 2019

(30) Foreign Application Priority Data

Jul. 10, 2017 (KR) .................. 10-2017-0087248

(51) Int. Cl.
*H01L 51/00* (2006.01)
*C07D 251/24* (2006.01)
(Continued)

(52) U.S. Cl.
CPC ........ *H01L 51/0067* (2013.01); *C07D 251/24* (2013.01); *C07D 405/10* (2013.01);
(Continued)

(58) Field of Classification Search
None
See application file for complete search history.

(56) References Cited

U.S. PATENT DOCUMENTS

2004/0251816 A1   12/2004   Leo et al.
2012/0214993 A1   8/2012    Aihara et al.
(Continued)

FOREIGN PATENT DOCUMENTS

EP    2966706 A2     1/2016
JP    2009224512 A   10/2009
(Continued)

OTHER PUBLICATIONS

IUPAC definition of aryl group, 1 page, Source, PAC, 1995, 67, 1320 (Glossary of class names of organic compounds and reactivity intermediates based on structure (IUPAC Recommendations)). (Year: 1995).*

*Primary Examiner* — Robert S Loewe
(74) *Attorney, Agent, or Firm* — Dentons US LLP

(57) ABSTRACT

The present disclosure relates to a cyclic compound represented by the following Chemical Formula 1, and an organic light emitting device including the same. The cyclic compound used as a material of an organic material layer of the organic light emitting device provides a low driving voltage and an improved lifetime characteristic of the organic light emitting device.

(Continued)

[Chemical Formula 1]

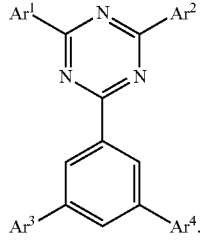

6 Claims, 1 Drawing Sheet

(51) Int. Cl.
*C07D 405/10* (2006.01)
*H01L 51/50* (2006.01)
(52) U.S. Cl.
CPC .......... H01L 51/0073 (2013.01); H01L 51/50 (2013.01); H01L 51/5012 (2013.01); *H01L 51/5056* (2013.01); *H01L 51/5072* (2013.01); *H01L 51/5088* (2013.01); *H01L 51/5092* (2013.01)

(56) References Cited

U.S. PATENT DOCUMENTS

| | | | |
|---|---|---|---|
| 2014/0330013 A1 | 11/2014 | Aihara et al. | |
| 2014/0367656 A1 | 12/2014 | Kim et al. | |
| 2015/0200373 A1* | 7/2015 | Cho | C09B 57/10 257/40 |
| 2015/0243895 A1* | 8/2015 | Lim | H01L 51/0054 257/40 |
| 2015/0243908 A1* | 8/2015 | Lee | C07D 405/10 257/40 |
| 2015/0329544 A1 | 11/2015 | Aihara et al. | |
| 2015/0364693 A1 | 12/2015 | Ito et al. | |
| 2015/0380662 A1 | 12/2015 | Kim et al. | |
| 2016/0020404 A1 | 1/2016 | Ito et al. | |
| 2016/0028021 A1 | 1/2016 | Zeng et al. | |
| 2016/0056388 A1 | 2/2016 | Oka et al. | |
| 2016/0093808 A1 | 3/2016 | Adamovich et al. | |
| 2016/0211454 A1 | 7/2016 | Kim et al. | |
| 2016/0218297 A1 | 7/2016 | Ito et al. | |
| 2016/0260901 A1 | 9/2016 | Kim et al. | |
| 2017/0092873 A1* | 3/2017 | Kang | H01L 51/0054 |
| 2017/0155049 A1* | 6/2017 | Kim | H01L 51/0052 |
| 2017/0244043 A1* | 8/2017 | Kim | H01L 51/0052 |
| 2018/0066180 A1 | 3/2018 | Huh et al. | |
| 2018/0337341 A1* | 11/2018 | Heo | C07D 307/91 |

FOREIGN PATENT DOCUMENTS

| | | |
|---|---|---|
| JP | 2010095452 A | 4/2010 |
| JP | 2010134121 A | 6/2010 |
| JP | 2011063584 A | 3/2011 |
| JP | 2012254976 A | 12/2012 |
| JP | 2012256882 A | 12/2012 |
| JP | 2014125449 A | 7/2014 |
| JP | 2015034148 A | 2/2015 |
| JP | 2015074649 A | 4/2015 |
| JP | 2015126140 A | 7/2015 |
| JP | 2015199681 A | 11/2015 |
| JP | 2015199683 A | 11/2015 |
| JP | 2015205235 A | 11/2015 |
| JP | 5829388 B2 | 12/2015 |
| JP | 2016152239 A | 8/2016 |
| KR | 1020000051826 A | 8/2000 |
| KR | 1020100131939 A | 12/2010 |
| KR | 1020140055546 A | 5/2014 |
| KR | 10-2015-0101923 A | 9/2015 |
| KR | 1020150120875 A | 10/2015 |
| KR | 1020150129282 A | 11/2015 |
| KR | 1020150131998 A | 11/2015 |
| KR | 1020160066339 A | 6/2016 |
| KR | 1020160090262 A | 7/2016 |
| KR | 1020160126862 A | 11/2016 |
| KR | 1020160127503 A | 11/2016 |
| KR | 1020160141672 A | 12/2016 |
| KR | 1020160149527 A | 12/2016 |
| KR | 1020160150185 A | 12/2016 |
| KR | 10-2017-0030925 A | 3/2017 |
| KR | 1020170049291 A | 5/2017 |
| KR | 1020170090139 A | 8/2017 |
| WO | 2003012890 A2 | 2/2003 |
| WO | 2011021689 A1 | 2/2011 |
| WO | 2013069762 A1 | 5/2013 |
| WO | 2013191177 A1 | 12/2013 |
| WO | 2014171541 A1 | 10/2014 |
| WO | 2014208755 A1 | 12/2014 |
| WO | 2015008866 A1 | 1/2015 |
| WO | 2015125814 A1 | 8/2015 |
| WO | 2016002921 A1 | 1/2016 |
| WO | WO-2017043908 A1 * | 3/2017 ............ C07D 209/82 |
| WO | WO-2017099490 A1 * | 6/2017 ............ C07D 209/82 |

* cited by examiner

[FIG. 1]
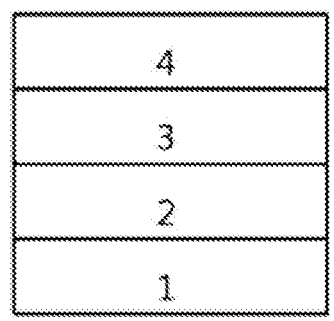
[FIG. 2]
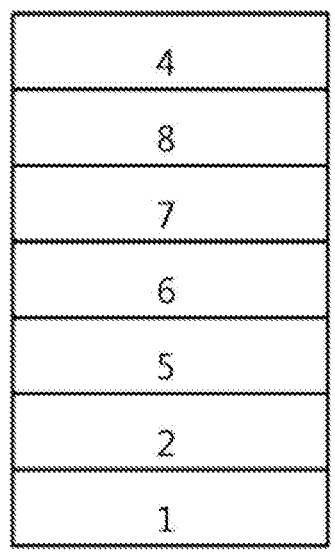

HETEROCYCLIC COMPOUND AND ORGANIC LIGHT EMITTING DEVICE COMPRISING THE SAME

TECHNICAL FIELD

CROSS-REFERENCE TO RELATED APPLICATION(S)

This application is a National Stage Application of International Application No. PCT/KR2018/004954 filed on Apr. 27, 2018, which claims the benefit of filing date of Korean Patent Application No. 10-2017-0087248 filed with Korean Intellectual Property Office on Jul. 10, 2017, the entire content of which is incorporated herein by reference.

The present disclosure relates to a heterocyclic compound having a novel structure and to an organic light emitting device including the same.

BACKGROUND ART

In general, an organic light emitting phenomenon refers to a phenomenon where electrical energy is converted into light energy by using an organic material. The organic light emitting device using the organic light emitting phenomenon has characteristics such as a wide viewing angle, excellent contrast, a fast response time, and excellent luminance, driving voltage, and response speed, and many studies have proceeded thereon.

The organic light emitting device generally has a structure which includes an anode, a cathode, and an organic material layer interposed between the anode and the cathode. The organic material layer may have a multilayered structure that includes different materials in order to enhance efficiency and stability of the organic light emitting device, and for example, the organic material layer may be formed of a hole injection layer, a hole transport layer, a light emitting layer, an electron transport layer, an electron injection layer, and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state.

There is a continuing need for the development of new materials for the organic materials used in such organic light emitting devices.

PRIOR ART LITERATURE

Patent Literature (Patent Literature 1) Korean Patent Laid-open Publication No. 10-2000-0051826

DETAILED DESCRIPTION OF THE INVENTION

Technical Problem

It is an object of the present disclosure to provide a heterocyclic compound having a novel structure.

It is another object of the present disclosure to provide an organic light emitting device including the heterocyclic compound having a novel structure.

Technical Solution

The present disclosure provides a compound represented by the following Chemical Formula 1:

[Chemical Formula 1]

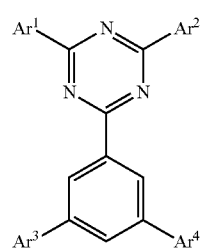

wherein, in Chemical Formula 1, $Ar^1$ and $Ar^2$ are each independently a substituted or unsubstituted aryl group having 6 to 60 carbon atoms, $Ar^3$ is a substituted or unsubstituted aryl group having 10 to 60 carbon atoms, or a substituted or unsubstituted heteroaryl group having 10 to 60 carbon atoms and containing at least one of O, N, Si, and S, and $Ar^4$ is an aryl group having 6 to 60 carbon atoms and substituted with a cyano group.

The present disclosure also provides an organic light emitting device including: a first electrode; a second electrode provided at a side opposite to the first electrode; and at least one layer of the organic material layers provided between the first electrode and the second electrode, wherein the at least one layer of the organic material layers includes the compound represented by Chemical Formula 1.

Advantageous Effects

The compound represented by Chemical Formula 1 can be used as a material of an organic material layer of an organic light emitting device, and can achieve a low driving voltage and/or an improvement of the lifetime characteristic when applied to the organic light emitting device. The compound represented by Chemical Formula 1 can be used as hole injection, hole transport, hole injection and transport, light emitting, electron transport, or electron injection materials, and in particular can be used as an electron injection and/or electron transport material.

BRIEF DESCRIPTION OF DRAWINGS

FIG. 1 shows an example of an organic light emitting device including a substrate 1, an anode 2, a light emitting layer 3, and a cathode 4.

FIG. 2 shows an example of an organic light emitting device including a substrate 1, an anode 2, a hole injection layer 5, a hole transport layer 6, a light emitting layer 7, an electron transport layer 8, and a cathode 4.

DETAILED DESCRIPTION OF THE EMBODIMENTS

Hereinafter, the present disclosure will be described in more detail to facilitate understanding of the present disclosure.

The present disclosure provides a compound represented by Chemical Formula 1.

In the present specification, the notation

represents a bond connected to another compound.

In the present specification, a non-bond means a case where no chemical bond is present in a part represented by $X^1$. For example, when $X^1$ in Chemical Formula 1-1 is a non-bond, the structure of Chemical Formula 1-1 is the same as the structure in which $Ar^3$ in Chemical Formula 1 is a monovalent group derived from 9,9-diphenylfluorene.

In the present specification, a single bond means the case in which no separate atom is present at a part represented by $X^1$. For example, if $X^1$ in Chemical Formula 1 is a single bond, the structure of Chemical Formula 1-1 is the same as the structure in which $Ar^3$ in Chemical Formula 1 is a monovalent group derived from spiro[fluorene-9,9'-fluorene].

As used herein, the term "substituted or unsubstituted" means being unsubstituted or substituted by $R^a$, wherein $R^a$ may be deuterium, a halogen, a cyano group, a nitro group, an amino group, an alkyl group having 1 to 40 carbon atoms, a haloalkyl group having 1 to 40 carbon atoms containing at least one of O, N, Si, and S, a substituted or unsubstituted heteroalkyl group having 1 to 40 carbon atoms containing at least one of O, N, Si, and S, a substituted or unsubstituted heterohaloalkyl group having 1 to 40 carbon atoms containing at least one of O, N, Si, and S, or an alkenyl group having 2 to 40 carbon atoms.

In the present specification, the halogen may be fluorine, chlorine, bromine, or iodine.

In the present specification, an alkyl group having 1 to 40 carbon atoms may be a straight-chain, branched, or cyclic alkyl group. Specifically, the alkyl group having 1 to 40 carbon atoms may be a straight-chain alkyl group having 1 to 40 carbon atoms; a straight-chain alkyl group having 1 to 20 carbon atoms; a straight-chain alkyl group having 1 to 10 carbon atoms; a branched or cyclic alkyl group having 3 to 40 carbon atoms; a branched or cyclic alkyl group having 3 to 20 carbon atoms; or a branched or cyclic alkyl group having 3 to 10 carbon atoms. More specifically, the alkyl group having 1 to 40 carbon atoms may be a methyl group, an ethyl group, an n-propyl group, an iso-propyl group, an n-butyl group, an iso-butyl group, a t-butyl group, an n-pentyl group, an iso-pentyl group, a neo-pentyl group, a cyclohexyl group, or the like, but is not limited thereto.

In the present specification, a heteroalkyl group having 1 to 40 carbon atoms may be one in which at least one carbon of the alkyl group is independently substituted with O, N, Si, or S. As an example of the straight-chain alkyl group, the heteroalkyl group in which the $1^{st}$ carbon of an n-butyl group is substituted with O is an n-propoxy group, the heteroalkyl group substituted with N is an n-propylamino group, the heteroalkyl group substituted with Si is an n-propylsilyl group, and the heteroalkyl group substituted with S is an n-propylthio group. In addition, as an example of the branched alkyl group, the heteroalkyl group in which the $1^{st}$ carbon of a neopentyl group is substituted with O is a t-butoxy group, the heteroalkyl group substituted with N is a t-butylamino group, the heteroalkyl group substituted with Si is a t-butylsilyl group, and the heteroalkyl group substituted with S is a t-butylthio group. Further, as an example of the cyclic alkyl group, the heteroalkyl group in which the $2^{nd}$ carbon of a cyclohexyl group is substituted with O is a 2-tetrahydropyranyl group, the heteroalkyl group substituted with N is a 2-piperidinyl group, the heteroalkyl group substituted with Si is a 1-sila-cyclohexyl group, and the heteroalkyl group substituted with S is a 2-tetrahydrothiopyranyl group. Specifically, the heteroalkyl group having 1 to 40 carbon atoms may include a straight-chain, branched, or cyclic hydroxyalkyl group having 1 to 40 carbon atoms; a straight-chain, branched, or cyclic alkoxy group having 1 to 40 carbon atoms; a straight-chain, branched, or cyclic alkoxyalkyl group having 2 to 40 carbon atoms; a straight-chain, branched, chain or cyclic aminoalkyl group having 1 to 40 carbon atoms; a straight-chain, branched, or cyclic alkylamino group having 1 to 40 carbon atoms; a straight-chain, branched, or cyclic alkylaminoalkyl group having 1 to 40 carbon atoms; a straight-chain, branched, or cyclic silylalkyl(oxy) group having 1 to 40 carbon atoms; a straight-chain, branched, or cyclic alkyl(oxy)silyl group having 1 to 40 carbon atoms; a straight-chain, branched, or cyclic alkyl(oxy)silylalkyl(oxy) group having 1 to 40 carbon atoms; a straight-chain, branched, or cyclic mercaptoalkyl group having 1 to 40 carbon atoms; a straight-chain, branched, or cyclic alkylthio group having 1 to 40 carbon atoms; or a straight-chain, branched, or cyclic alkylthioalkyl group having 2 to 40 carbon atoms. More specifically, the heteroalkyl group having 1 to 40 carbon atoms may include a hydroxymethyl group, a methoxy group, an ethoxy group, an n-propoxy group, an iso-propoxy group, a t-butoxy group, a cycloheptoxy group, a methoxymethyl group, an iso-propoxymethyl group, a cyclohexylmethyl group, a 2-tetrahydropyranyl group, an aminomethyl group, a methylamino group, an n-propylamino group, a t-butylamino group, a methylaminopropyl group, a 2-piperidinyl group, an n-propylsilyl group, a trimethylsilyl group, a dimethylmethoxysilyl group, a t-butylsilyl group, a 1-sila-cyclohexyl group, an n-propylthio group, a t-butylthio group, a 2-tetrahydrothiopyranyl group, or the like. However, the present disclosure is not limited thereto.

In the present specification, an alkenyl group having 2 to 40 carbon atoms may be a straight-chain, branched, or cyclic alkenyl group. Specifically, the alkenyl group having 2 to 40 carbon atoms may include a straight-chain alkenyl group having 2 to 40 carbon atoms; a straight-chain alkenyl group having 2 to 20 carbon atoms; a straight-chain alkenyl group having 2 to 10 carbon atoms; a branched alkenyl group having 3 to 40 carbon atoms; a branched alkenyl group having 3 to 20 carbon atoms; a branched alkenyl group having 3 to 10 carbon atoms; a cyclic alkenyl group having 5 to 40 carbon atoms; a cyclic alkenyl group having 5 to 20 carbon atoms; or a cyclic alkenyl group having 5 to 10 carbon atoms. More specifically, the alkenyl group having 2 to 40 carbon atoms may include an ethenyl group, a propenyl group, a butenyl group, a pentenyl group, a cyclohexenyl group, or the like. However, the present disclosure is not limited thereto.

In the present specification, an aryl group having 6 to 60 carbon atoms may be a monocyclic aryl group or a polycyclic aryl group. Specifically, the aryl group having 6 to 60 carbon atoms may be a monocyclic or polycyclic aryl group having 6 to 30 carbon atoms, or a monocyclic or polycyclic aryl group having 6 to 20 carbon atoms. More specifically, the aryl group having 6 to 60 carbon atoms may be a phenyl group, a biphenyl group, a terphenyl group, or the like as the monocyclic aryl group, and the polycyclic aryl group may include a naphthyl group, an anthracenyl group, a phenanthryl group, a triphenylenyl group, a pyrenyl group, a perylenyl group, a chrycenyl group, a fluorenyl group, or the like.

Further, an aryl group having 6 to 60 carbon atoms may have a structure in which two or more selected from the group consisting of a monocyclic aryl group and a polycyclic aryl group are connected to each other. Specifically, the aryl group having 6 to 60 carbon atoms may have a structure in which a polycyclic aryl group and/or a monocyclic aryl group is connected to a polycyclic aryl group. More specifically, the aryl group having 6 to 60 carbon atoms may be a naphthylphenyl group, an anthracenylphenyl group, a phenanthrylphenyl group, a triphenylenylphenyl group, a pyrenylphenyl group, a perylenylphenyl group, a chrycenylphenyl group, a fluorenylphenyl group, a phenylnaphthyl group, a phenanthracenyl group, a phenylnaphthylphenyl group, or the like. However, the present disclosure is not limited thereto.

In the present specification, a fluorenyl group may be substituted, and two substituent groups may be linked with each other to form a spiro structure. In the case where the fluorenyl group is substituted,

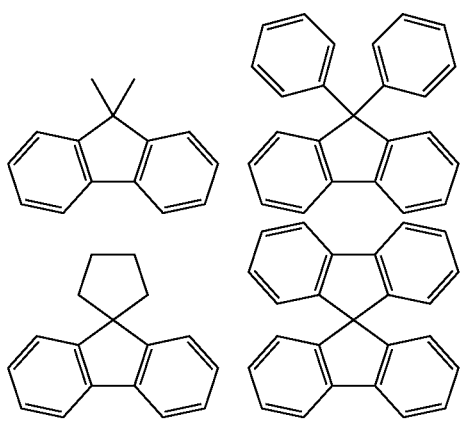

and the like can be formed. However, the structure is not limited thereto.

In the present specification, a heteroaryl group having 2 to 60 carbon atoms may be one in which at least one carbon of an aryl group is independently substituted with O, N, Si, or S. For example, the heteroaryl group in which the 9th carbon of a fluorenyl group is substituted with O is a dibenzofuranyl group, the heteroaryl group substituted with N is a carbazolyl group, the heteroaryl group substituted with Si is a 9-sila-fluorenyl group, and the heteroaryl group substituted with S is a dibenzothiophenyl group. Specifically, the heteroaryl group having 2 to 60 carbon atoms may be a heteroaryl group having 2 to 30 carbon atoms, or a heteroaryl group having 2 to 20 carbon atoms. More specifically, the heteroaryl group having 2 to 60 carbon atoms may include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but is not limited thereto.

In the present specification, an aryl group having 10 to 60 carbon atoms means an aryl group having 10 or more carbon atoms among the above-mentioned aryl groups having 6 to 60 carbon atoms, and a heteroaryl group having 10 to 60 carbon atoms means a heteroaryl group having 10 or more carbon atoms among the above-mentioned heteroaryl groups having 2 to 60 carbon atoms.

In Chemical Formula 1, $Ar^1$ and $Ar^2$ may each independently be a phenyl group or a biphenyl group.

In Chemical Formula 1, $Ar^3$ and $Ar^4$ may be different from each other.

Specifically, $Ar^3$ may be a monovalent group derived from an arene selected from the group consisting of naphthalene, biphenyl, terphenyl, triphenylene, phenanthrene, phenyl naphthalene, 9,9-dimethylfluorene, 9,9-diphenylfluorene, and spiro[fluorene-9,9'-fluorene], or a monovalent group derived from a heteroarene selected from the group consisting of spiro[fluorene-9,9'-xanthene] and spiro[fluorene-9,9'-thioxanthene].

Further, $Ar^4$ is an arene selected from the group consisting of benzene, naphthalene, biphenyl, terphenyl, triphenylene, phenanthrene, phenyl naphthalene, 9,9-dimethylfluorene, 9,9-diphenylfluorene, and spiro[fluorene-9,9'-fluorene], in which the arene may be a monovalent residue derived from an arene substituted with a cyano group.

More specifically, $Ar^4$ may be a substituent selected from the group consisting of the following substituent groups.

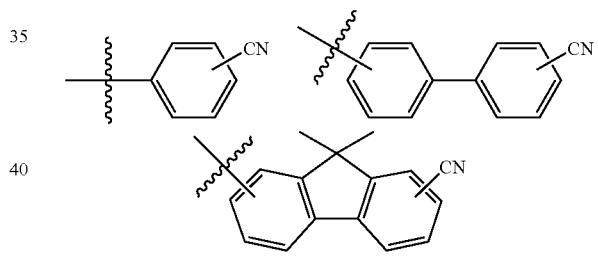

The compound represented by Chemical Formula 1 may be a compound selected from the group consisting of compounds represented by the following Chemical Formulae 1-1 and 1-2.

[Chemical Formula 1-1]

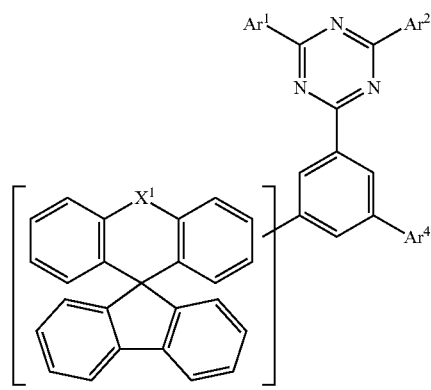

In Chemical Formula 1-1,
X¹ is a non-bond, a single bond, O, or S, and
Ar¹, Ar², and Ar⁴ are the same as defined in Chemical Formula 1.

[Chemical Formula 1-2]

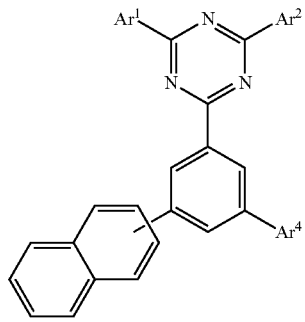

In Chemical Formula 1-2,
Ar¹, Ar², and Ar⁴ are the same as defined in Chemical Formula 1.

Ar¹, Ar², and Ar⁴ in Chemical Formulae 1-1 and 1-2 are the same as Ar¹, Ar², and Ar⁴ in Chemical Formulae 1, and specific examples of Ar¹, Ar², and Ar⁴ have been described in detail above, and thus a detailed description thereof will be omitted here.

The compound represented by Chemical Formula 1 may be selected from the group consisting of the following compounds.

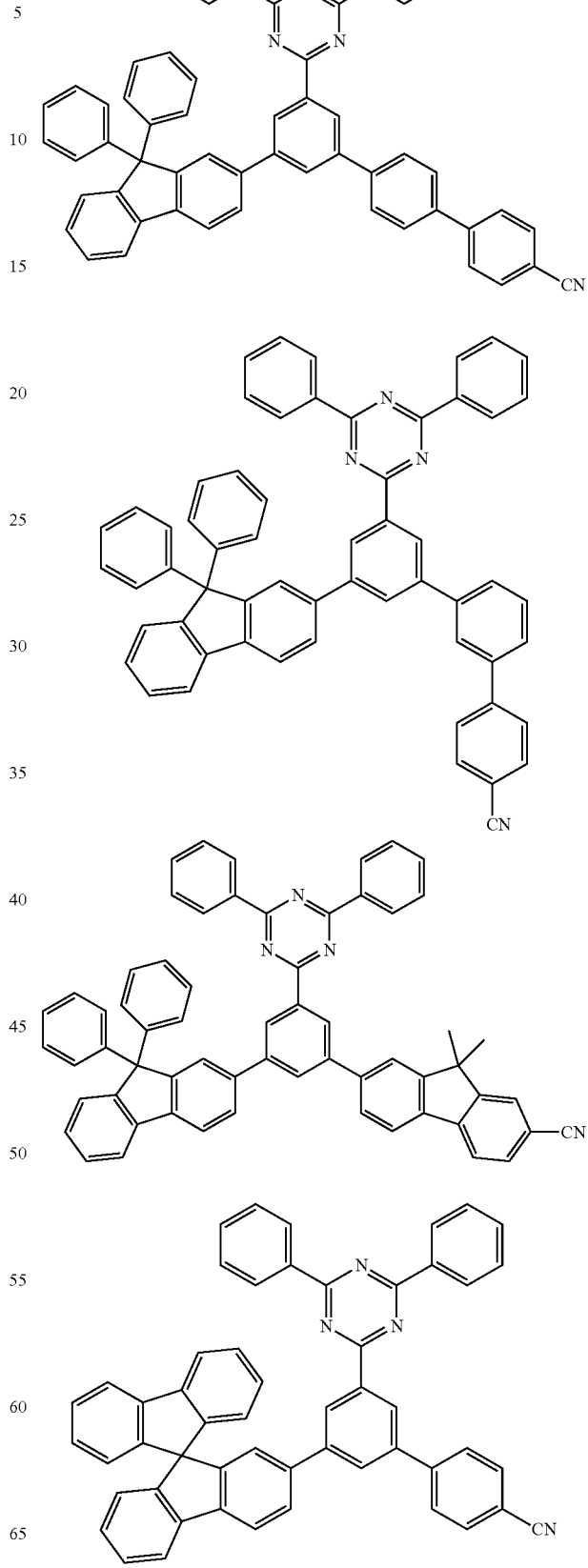

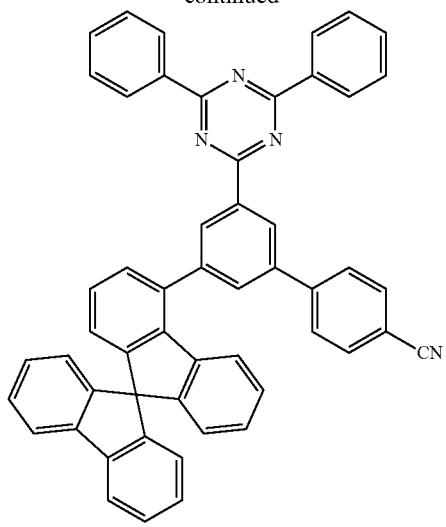
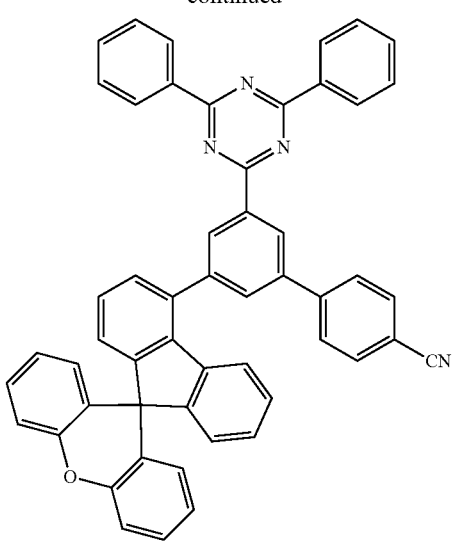
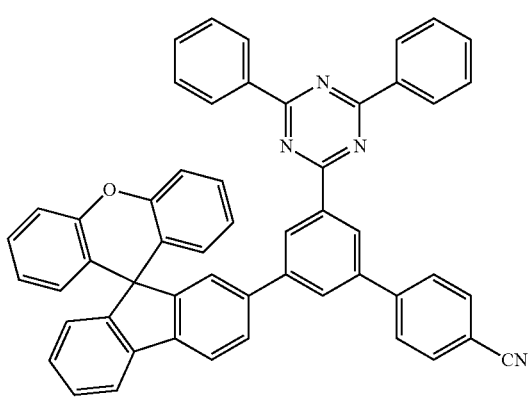
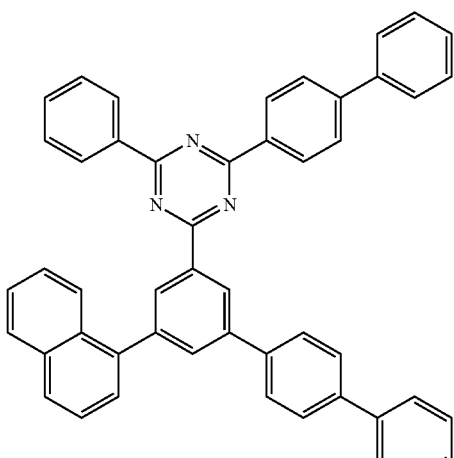
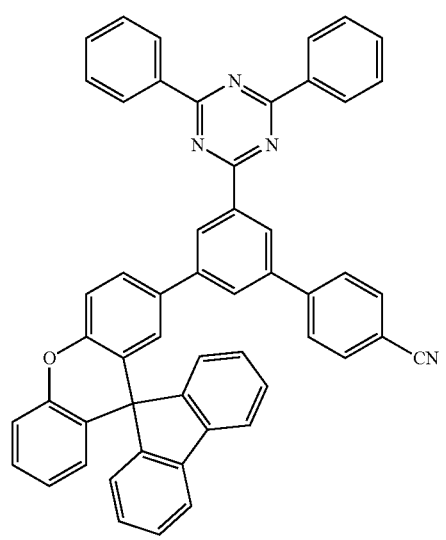
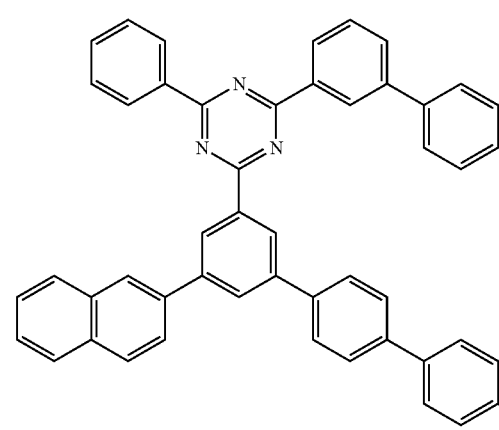

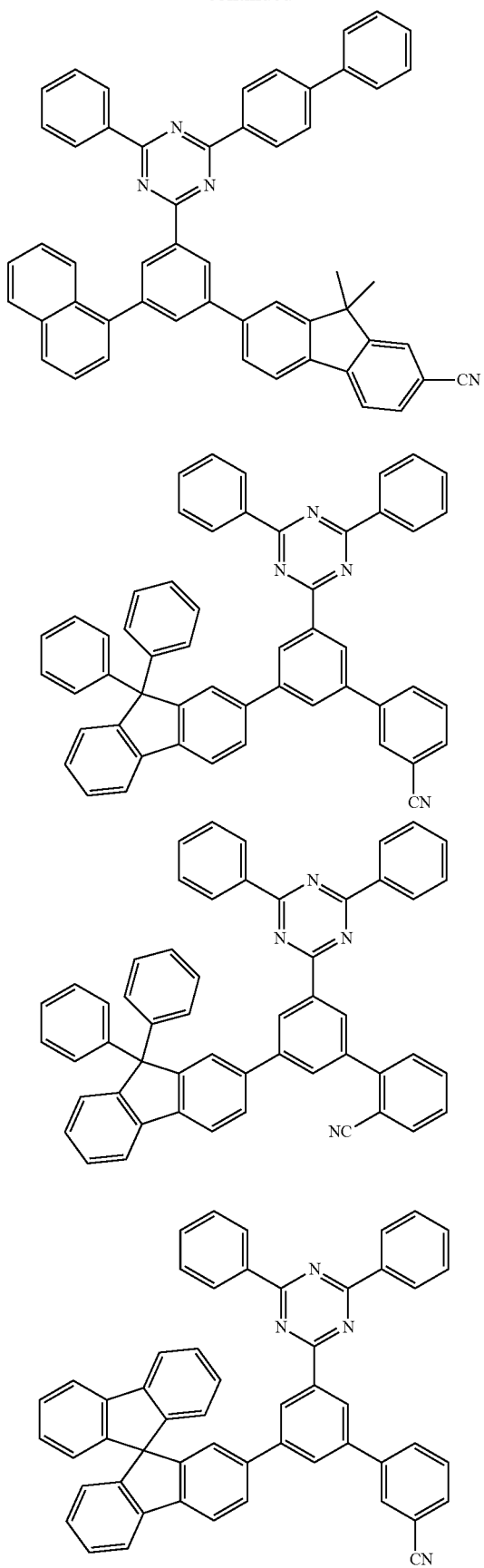

-continued

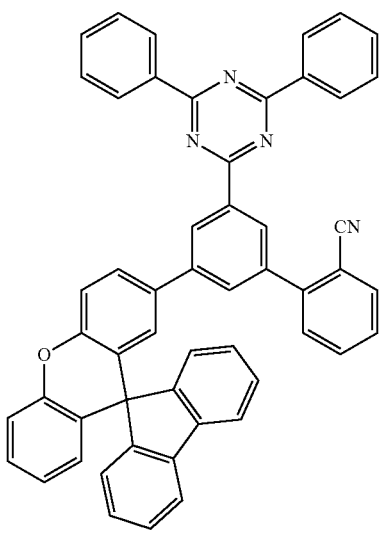

The compound represented by Chemical Formula 1 can be prepared by the preparation method as shown in the following Reaction Scheme 1. The above preparation method can be further specified in preparation examples described hereinafter.

[Reaction Scheme 1]

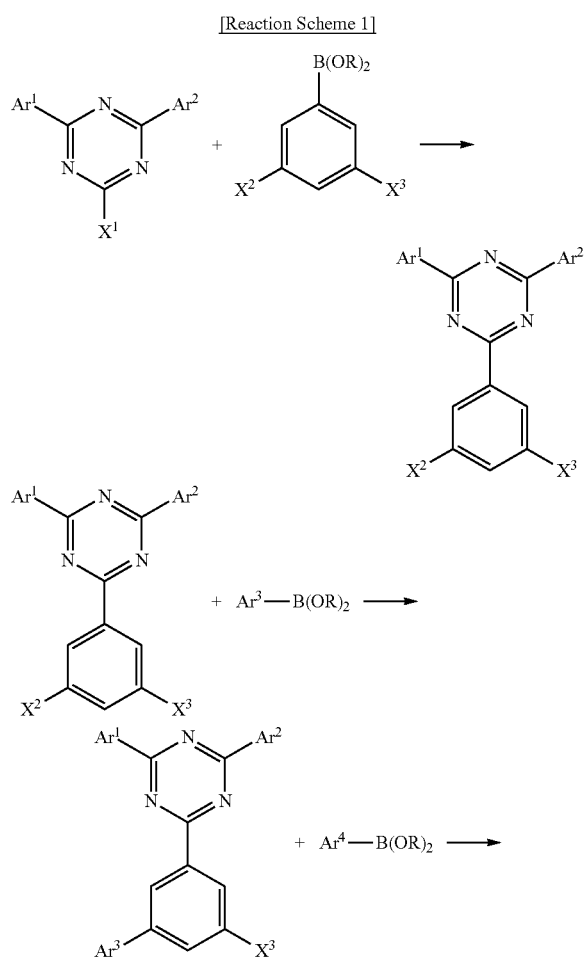

-continued

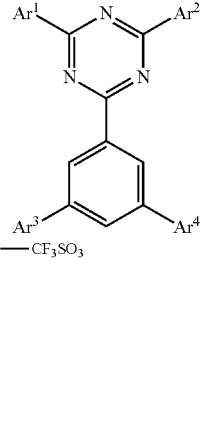

$X^1$~$X^3$ = —I, —Br, —Cl, —CH$_3$SO$_3$ or —CF$_3$SO$_3$

B(OR)$_2$ =

In addition, the present disclosure provides an organic light emitting device including the compound represented by Chemical Formula 1. In one example, the present disclosure provides an organic light emitting device including: a first electrode; a second electrode facing the first electrode; and at least one layer of organic material layers provided between the first electrode and the second electrode, wherein the at least one layer of the organic material layers include a compound represented by Chemical Formula 1.

The organic material layer of the organic light emitting device of the present disclosure may have a single layer structure, or it may have a multilayered structure in which two or more organic material layers are stacked. For example, the organic light emitting device of the present disclosure may have a structure including a hole injection layer, a hole transport layer, a light emitting layer, an electron transport layer, an electron injection layer, and the like as the organic material layer. However, the structure of the organic light emitting device is not limited thereto, and it may include a smaller number of organic layers.

Further, the organic material layer may include a hole injection layer, a hole transport layer, and a layer simultaneously performing hole injection and transport, wherein the hole injection layer, the hole transport layer, and the layer simultaneously performing hole injection and hole transport include a compound represented by Chemical Formula 1.

Further, the organic material layer may include a light emitting layer, wherein the light emitting layer may include a compound represented by Chemical Formula 1.

Further, the organic light emitting device according to the present disclosure may be a normal type of organic light emitting device in which an anode, at least one organic material layer, and a cathode are sequentially stacked on a substrate. Further, the organic light emitting device according to the present disclosure may be an inverted type organic light emitting device in which a cathode, at least one organic material layer, and an anode are sequentially stacked on a substrate. For example, the structure of an organic light emitting device according to an embodiment of the present disclosure is illustrated in FIGS. 1 and 2.

FIG. 1 shows an example of an organic light emitting device including a substrate 1, an anode 2, a light emitting layer 3, and a cathode 4. In such a structure, the compound represented by Chemical Formula 1 may be included in the light emitting layer.

FIG. 2 shows an example of an organic light emitting device including a substrate 1, an anode 2, a hole injection layer 5, a hole transport layer 6, a light emitting layer 7, an electron transport layer 8, and a cathode 4. In such a structure, the compound represented by Chemical Formula 1 may be included in at least one layer of the hole injection layer, the hole transport layer, the light emitting layer, and the electron transport layer.

The organic light emitting device according to the present disclosure may be manufactured by materials and methods known in the art, except that at least one layer of the organic material layers includes the compound represented by Chemical Formula 1. In addition, when the organic light emitting device includes a plurality of organic material layers, the organic material layers may be formed of the same material or different materials.

For example, the organic light emitting device according to the present disclosure can be manufactured by sequentially stacking a first electrode, an organic material layer, and a second electrode on a substrate. In this case, the organic light emitting device may be manufactured by depositing a metal, a metal oxide having conductivity, or an alloy thereof on the substrate using a PVD (physical vapor deposition) method such as a sputtering method or an e-beam evaporation method to form an anode, forming an organic material layer including the hole injection layer, the hole transport layer, the light emitting layer, and the electron transport layer thereon, and then depositing a material that can be used as the cathode thereon. In addition to such a method, the organic light emitting device may be manufactured by sequentially depositing a cathode material, an organic material layer, and an anode material on a substrate (International Publication WO2003/012890). However, the preparation method is not limited thereto.

In addition, the compound represented by Chemical Formula 1 may be formed into an organic layer by a solution coating method as well as a vacuum deposition method at the time of manufacturing an organic light emitting element. Herein, the solution coating method means spin coating, dip coating, doctor blading, inkjet printing, screen printing, a spray method, roll coating, or the like, but is not limited thereto.

For example, the first electrode is an anode and the second electrode is a cathode, or the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SNO_2$:Sb; conductive polymers such as poly(3-methylthiophene), poly[3,4-(ethylene-1,2-dioxy)thiophene] (PEDOT), polypyrrole, and polyaniline; and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection layer is a layer for injecting holes from the electrode, and the hole injection material is preferably a compound which has an ability to transport the holes, thus having a hole injecting effect in the anode, and an excellent hole injecting effect to the light emitting layer or the light emitting material, and prevents movement of an exciton generated in the light emitting layer to the electron injection layer or the electron injection material, and has an excellent thin film forming ability. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymers, and the like, but are not limited thereto.

The hole transport layer is a layer that receives holes from a hole injection layer and transports the holes to the light emitting layer. The hole transport material is suitably a material having high mobility to the holes, and may receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The light emitting layer is a layer which emits light in the visible light region by combining holes and electrons respectively transported from the hole transport layer and the electron transport layer. Such light emitting layer may include a host material and a dopant material. The host material may be a fused aromatic ring derivative, a heterocycle-containing compound, or the like. Specific examples of the fused aromatic ring derivatives include anthracene derivatives, pyrene derivatives, naphthalene derivatives, pentacene derivatives, phenanthrene compounds, and fluoranthene compounds. Examples of heterocyclic compounds include carbazole derivatives, dibenzofuran derivatives, ladder-type furan compounds, pyrimidine derivatives, and the like, but are not limited thereto.

Examples of the dopant material include aromatic amine derivatives, styrylamine compounds, boron complexes, fluoranthene compounds, metal complexes, and the like. Specific examples of the aromatic amine derivatives include substituted or unsubstituted fused aromatic ring derivatives having an arylamino group, and examples thereof include pyrene, anthracene, chrysene, and periflanthene having the arylamino group, and the like, and the styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transport layer is a layer which receives the electrons from the electron injection layer or the cathode and transports the electrons to the light emitting layer, and the electron transport material may include a compound represented by Chemical Formula 1. The compound represented by Chemical Formula 1 has high mobility to the electrons, and can receive electrons well from the cathode and thus transfer the electrons to the light emitting layer.

The electron transport layer may further include another electron transport material known in the art to which the present invention belongs, in addition to the compound represented by Chemical Formula 1. Specific examples of such electron transport material include include an 8-hydroxyquinoline Al complex, a complex including Alq$_3$, an organic radical compound, a hydroxyflavone-metal complex, and the like, but are not limited thereto.

The electron injection layer is a layer injecting the electrons from the electrode, and a compound which has an ability to transport the electrons, an electron injecting effect from the cathode, and an excellent electron injecting effect to the light emitting layer or the light emitting material, that prevents movement of an exciton generated in the light emitting layer to the hole injection layer, and has an excellent thin film forming ability, is preferable. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone, and the like, and their derivatives, a metal complex compound, a nitrogen-containing 5-membered cycle derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris (2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

On the other hand, the organic material layer formed of the compound represented by Chemical Formula 1 has excellent capability of receiving electrons and transferring the electrons to the light emitting layer. Therefore, the organic light emitting device may include an organic layer including a compound represented by Chemical Formula 1 that performs electron injection and electron transport at the same time. Such a layer can replace the electron transport layer and the electron injection layer of the present disclosure and perform the function of the two organic material layers in one organic material layer.

The electron injection and transport layer may further include another electron transport material or electron injection material known in the art to which the present disclosure belongs, in addition to the compound represented by Chemical Formula 1. Since the specific types of the electron transport material and the electron injection material have been described above, a detailed description thereof will be omitted here.

The organic light emitting device according to the present disclosure may be a front emission type, a rear emission type, or a double side emission type according to the used material.

In addition, the compound represented by Chemical Formula 1 may be included in an organic solar cell or an organic transistor in addition to an organic light emitting device.

The preparation of the compound represented by Chemical Formula 1 and the organic light emitting device including the same will be described in detail in the following examples. However, these examples are presented for illustrative purposes only, and the scope of the present disclosure is not limited thereto.

Synthesis Example 1: Synthesis of Heterocyclic Compound

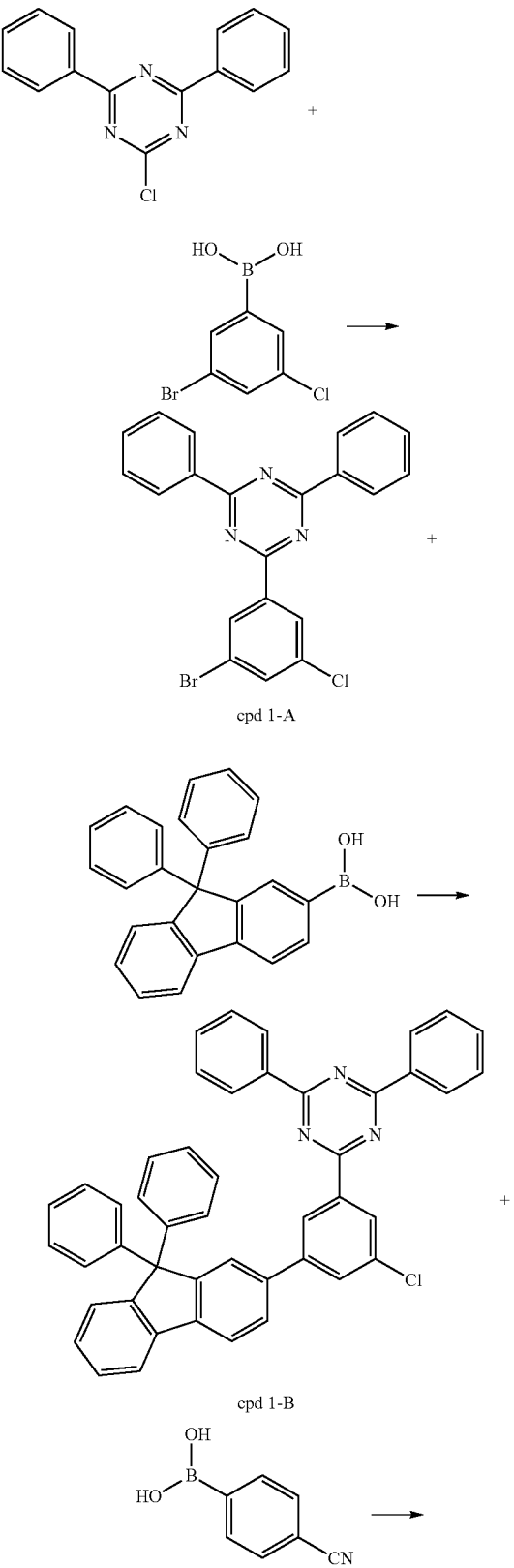

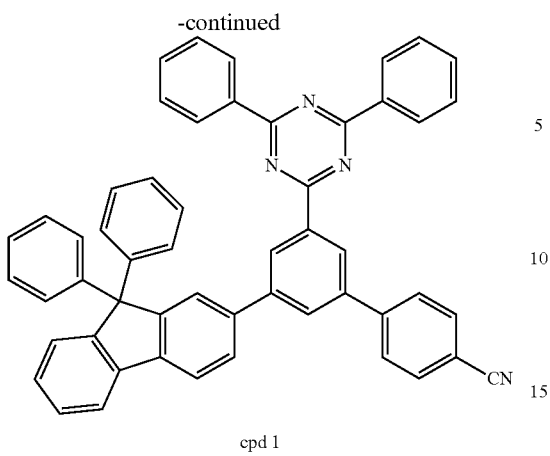

cpd 1

2-chloro-4,6-diphenyl-1,3,5-triazine (20.0 g, 74.7 mmol), (3-bromo-5-chlorophenyl)boronic acid (17.6 g, 74.7 mmol), and potassium carbonate (20.6 g, 149.4 mmol) were added to THF (250 mL) under a nitrogen stream, and the mixture was heated and stirred. Tetrakis(triphenylphosphine)palladium(0) (2.59 g, 2.24 mmol) was added thereto, and the mixture was heated and stirred for 5 hours. After cooling to room temperature, ethanol slurry purification was carried out to prepare the compound 1-A (cpd 1-A, 29 g, yield 91.9%) (MS:[M+H]$^+$=422).

The compound 1-A (cpd 1-A, 29 g, 68.6 mmol), (9,9-diphenyl-9H-fluoren-2-yl)boronic acid (24.8 g, 68.6 mmol), and potassium carbonate (19.0 g, 137.2 mmol) were added to THF (300 mL) under a nitrogen stream, and the mixture was heated and stirred. Tetrakis(triphenylphosphine)palladium(0) (2.38 g, 2.06 mmol) was added thereto, and the mixture was heated and stirred for 3 hours. After cooling to room temperature, ethanol slurry purification was carried out to prepare the compound 1-B (cpd 1-B, 41 g, yield 91.1%) (MS:[M+H]$^+$=660).

The compound 1-B (cpd 1-B, 41 g, 62.1 mmol), (4-cyanophenyl)boronic acid (9.1 g, 62.1 mmol), and potassium carbonate (17.2 g, 124.2 mmol) were added to THF (400 mL) under a nitrogen stream, and the mixture was heated and stirred. Potassium acetate (0.28 g, 1.24 mmol) and S-phos(2-dicyclohexylphosphino-2',6'-dimethoxybiphenyl, 1.01 g, 2.48 mmol) ligands were added thereto, and the mixture was heated and stirred for 2 hours. After cooling to room temperature, ethanol slurry purification was carried out to prepare the compound 1 (cpd 1, 42 g, yield 93.0%) (MS:[M+H]$^+$=727).

Synthesis Example 2: Synthesis of Heterocyclic Compound

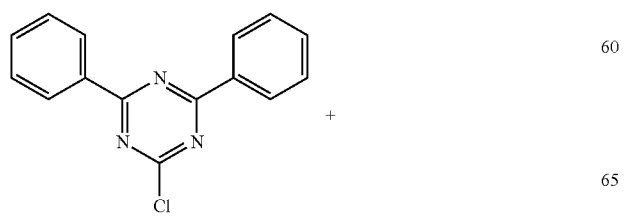

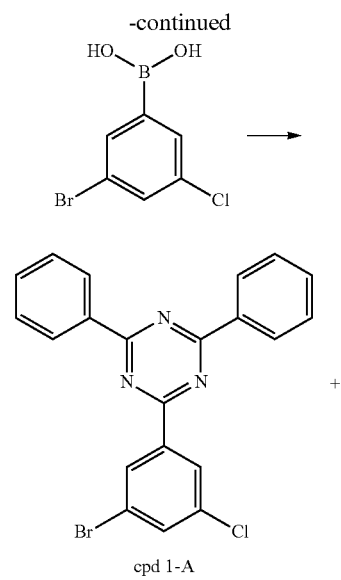

cpd 1-A

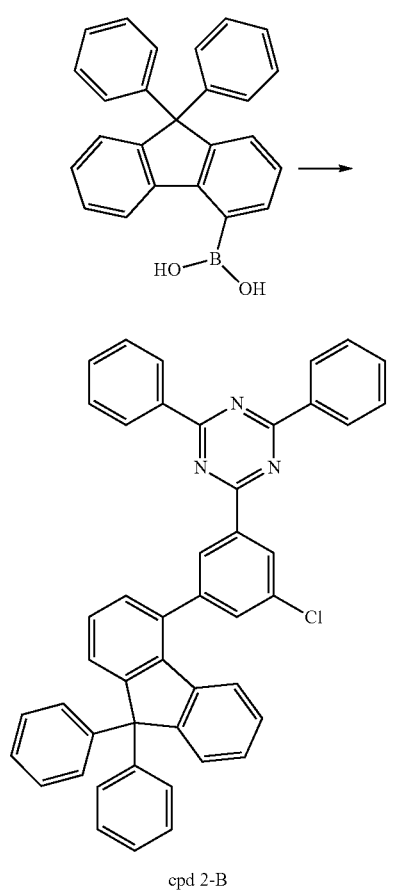

cpd 2-B

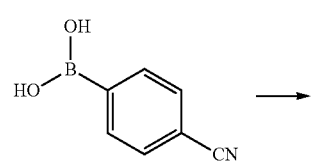

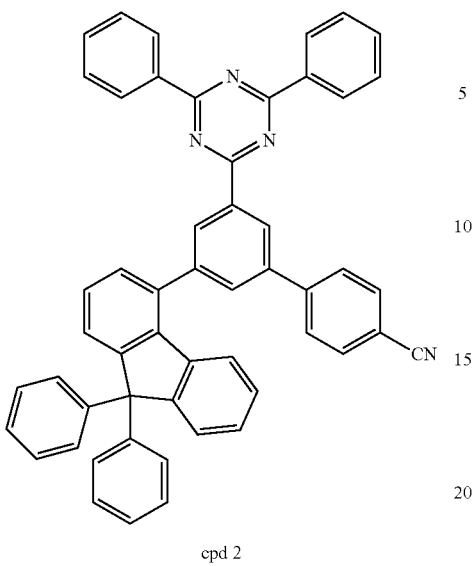

cpd 2

The compound 2-B (cpd 2-B) was prepared in the same manner as in Synthesis Example 1, except that (9,9-diphenyl-9H-fluoren-4-yl)boronic acid was used instead of (9,9-diphenyl-9H-fluoren-2-yl)boronic acid (MS:[M+H]+=660).

The compound 2 (cpd 2) was prepared in the same manner as in Synthesis Example 1, except that the compound 2-B (cpd 2-B) was used instead of the compound 1-B (cpd 1-B) (MS:[M+H]+=727).

Synthesis Example 3: Synthesis of Heterocyclic Compound

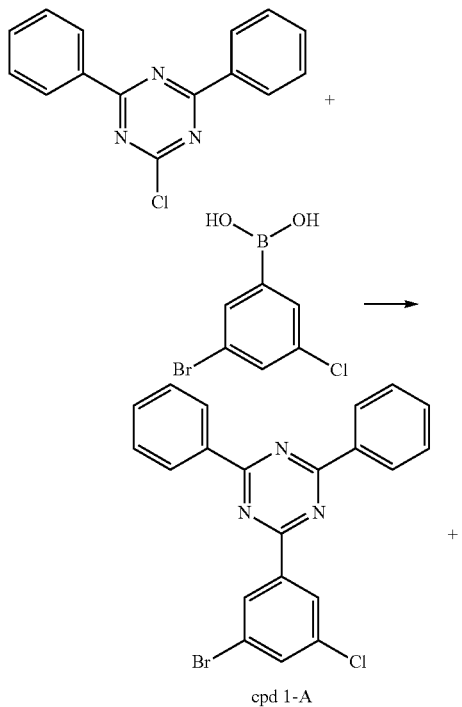

cpd 1-A

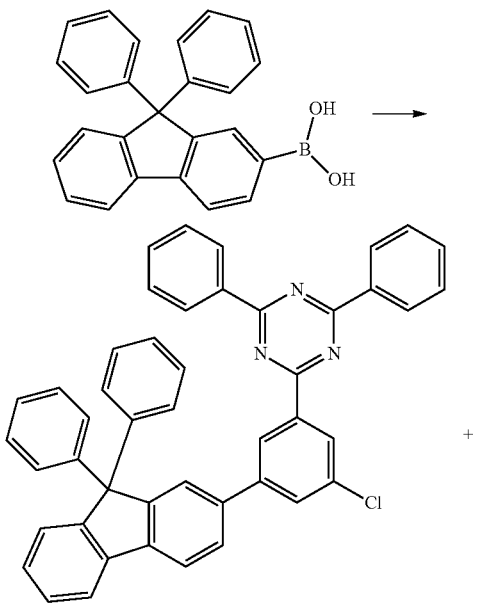

cpd 1-B

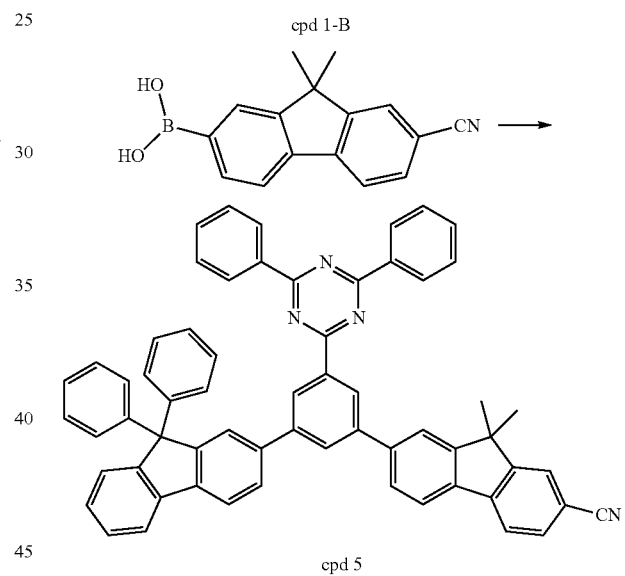

cpd 5

The compound 5 (cpd 5) was prepared in the same manner as in Synthesis Example 1, except that (7-cyano-9,9-dimethyl-9H-fluoren-2-yl)boronic acid was used instead of (4-cyanophenyl) boronic acid (MS:[M+H]+=843).

Synthesis Example 4: Synthesis of Heterocyclic Compound

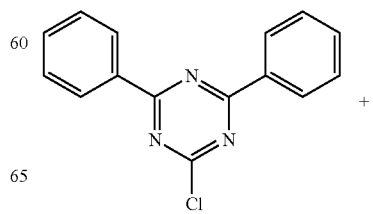

-continued

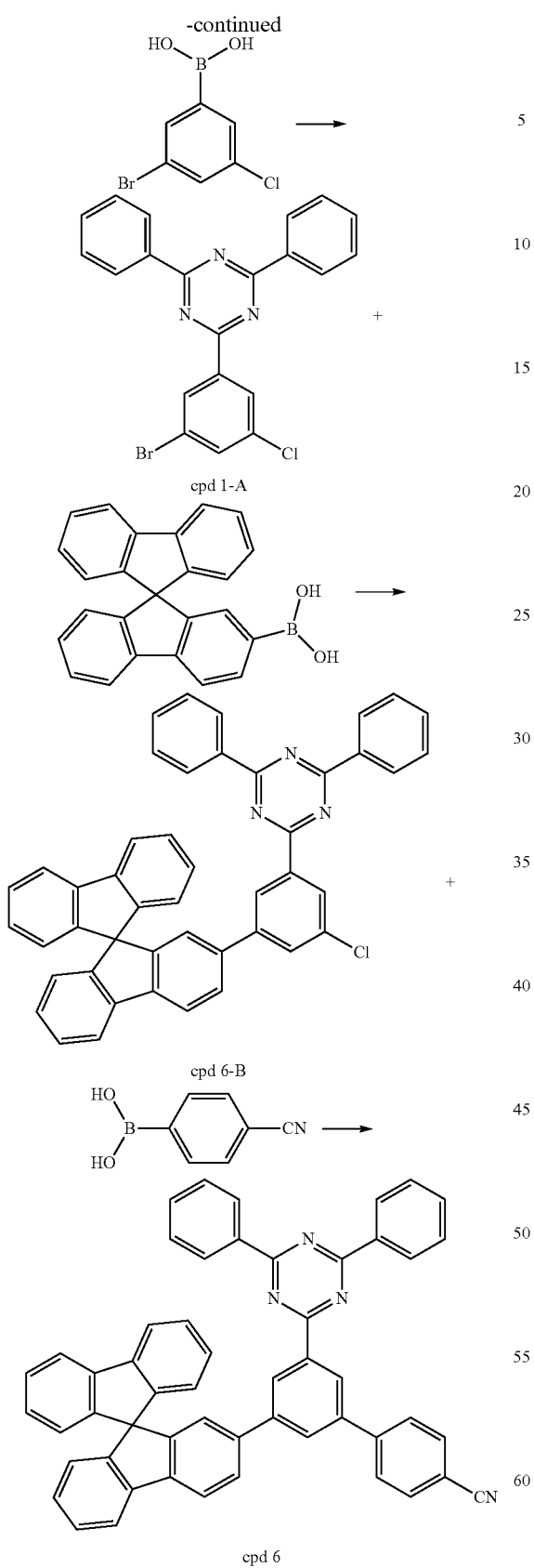

The compound 6-B (cpd 6-B) was prepared in the same manner as in Synthesis Example 1, except that spiro[fluo-rene-9,9'-fluorene]-2-ylboronic acid was used instead of (9,9-diphenyl-9H-fluoren-2-yl)boronic acid (MS:[M+H]+=658).

The compound 6 (cpd 6) was prepared in the same manner as in Synthesis Example 1, except that a compound 6-B (cpd 6-B) was used instead of a compound 1-B (cpd 1-B) (MS:[M+H]$^+$=725).

Synthesis Example 5: Synthesis of Heterocyclic Compound

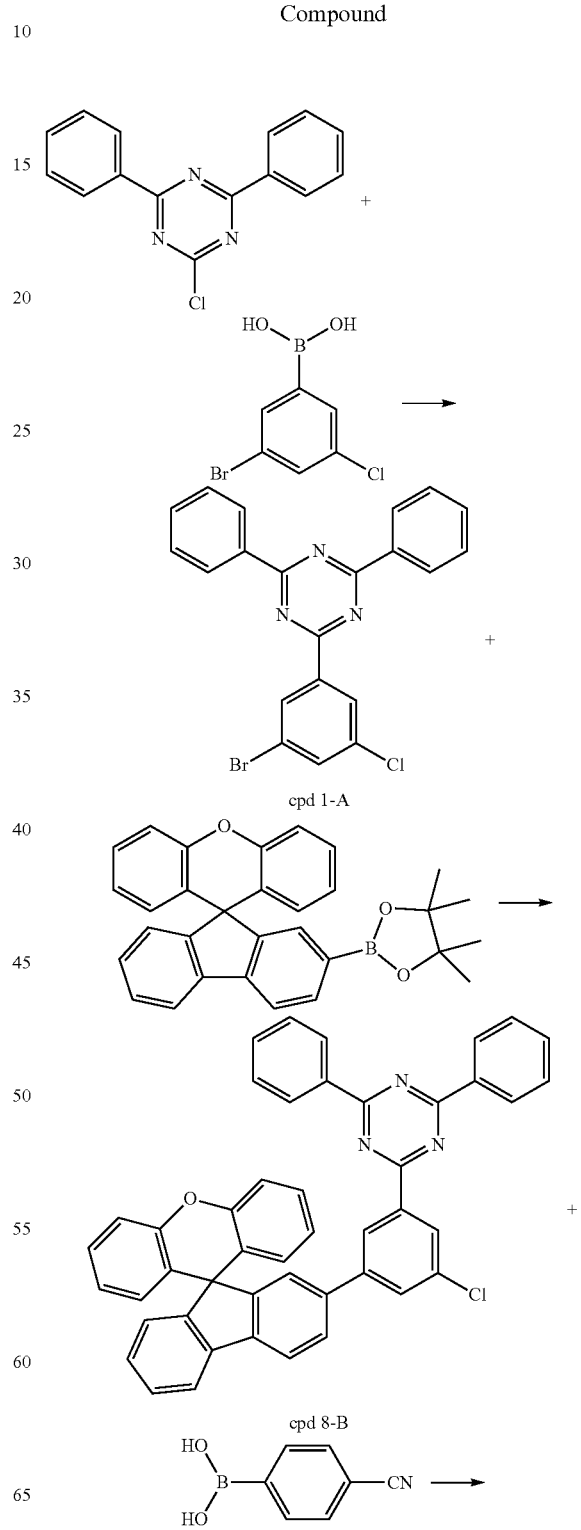

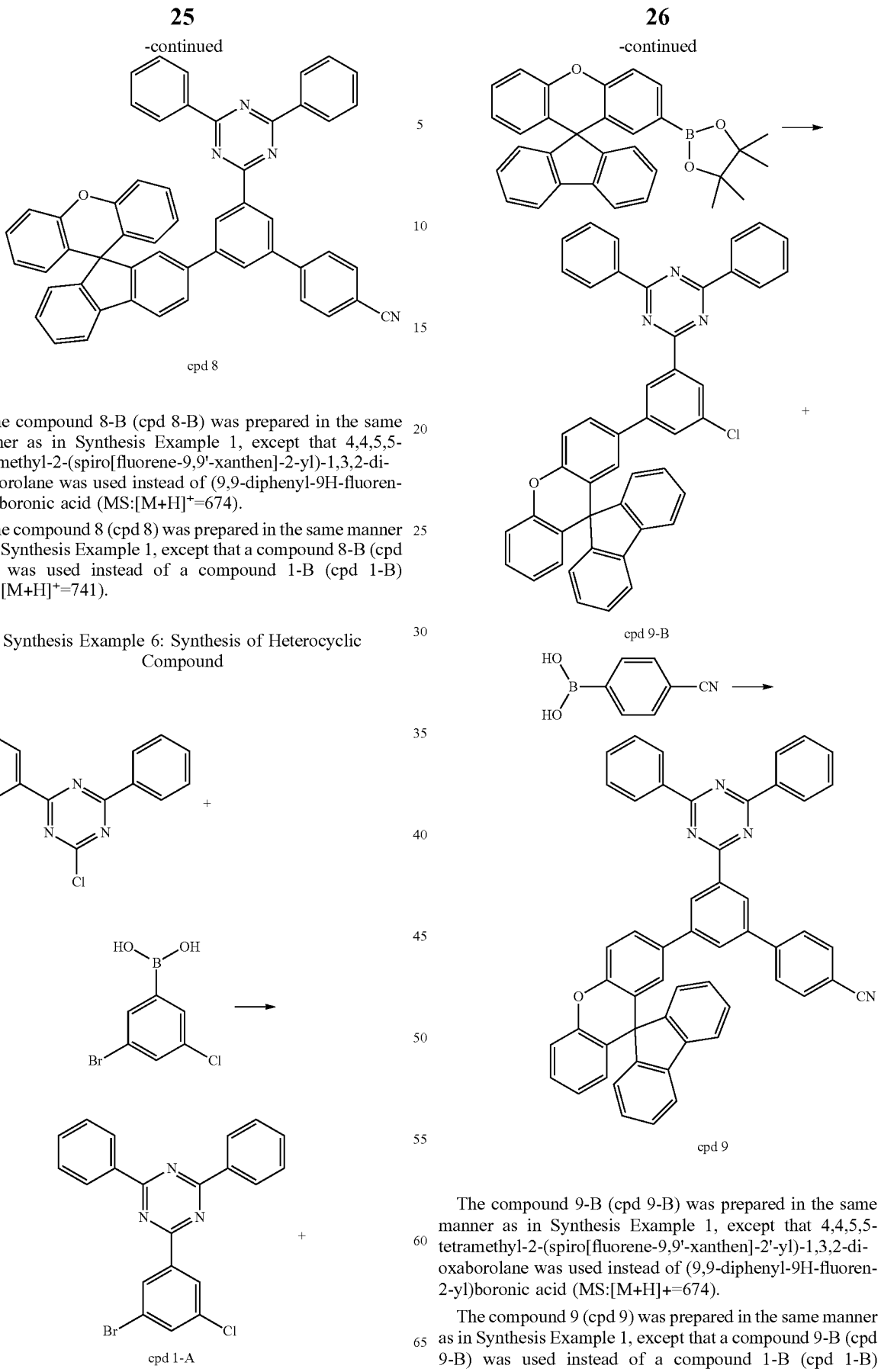

The compound 8-B (cpd 8-B) was prepared in the same manner as in Synthesis Example 1, except that 4,4,5,5-tetramethyl-2-(spiro[fluorene-9,9'-xanthen]-2-yl)-1,3,2-dioxaborolane was used instead of (9,9-diphenyl-9H-fluoren-2-yl)boronic acid (MS:[M+H]$^+$=674).

The compound 8 (cpd 8) was prepared in the same manner as in Synthesis Example 1, except that a compound 8-B (cpd 8-B) was used instead of a compound 1-B (cpd 1-B) (MS:[M+H]$^+$=741).

Synthesis Example 6: Synthesis of Heterocyclic Compound

The compound 9-B (cpd 9-B) was prepared in the same manner as in Synthesis Example 1, except that 4,4,5,5-tetramethyl-2-(spiro[fluorene-9,9'-xanthen]-2'-yl)-1,3,2-dioxaborolane was used instead of (9,9-diphenyl-9H-fluoren-2-yl)boronic acid (MS:[M+H]+=674).

The compound 9 (cpd 9) was prepared in the same manner as in Synthesis Example 1, except that a compound 9-B (cpd 9-B) was used instead of a compound 1-B (cpd 1-B) (MS:[M+H]$^+$=741).

Synthesis Example 7: Synthesis of Heterocyclic Compound

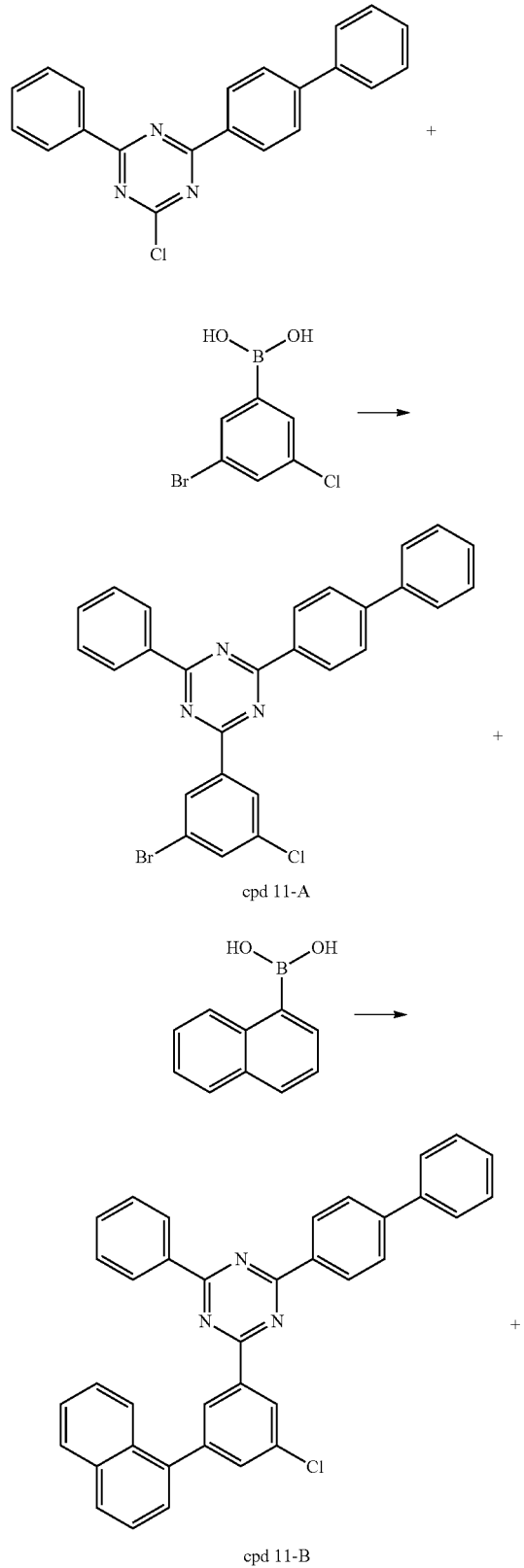

cpd 11-A cpd 11-B

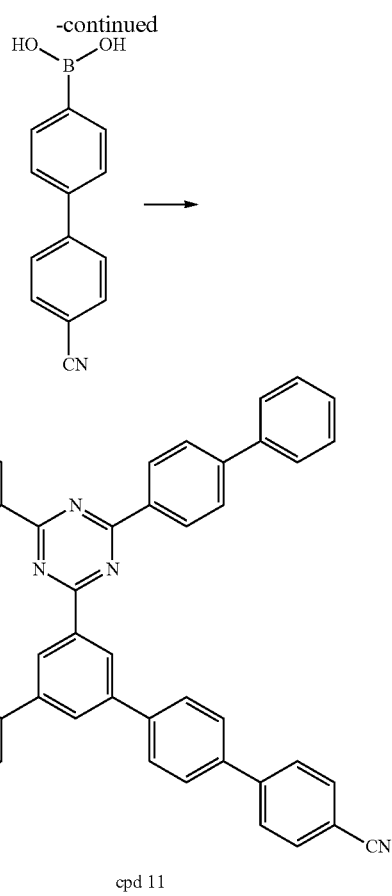

cpd 11

The compound 11-A (cpd 11-A) was prepared in the same manner as in Synthesis Example 1, except that 2-([1,1'-biphenyl]-4-yl)-4-chloro-6-phenyl-1,3,5-triazine was used instead of 2-chloro-4,6-diphenyl-1,3,5-triazine (MS:[M+H]$^+$=498).

The compound 11-B (cpd 11-B) was prepared in the same manner as in Synthesis Example 1, except that a compound 11-A (cpd 11-A) was used instead of a compound 1-A (cpd 1-A), and naphthalene-1-ylboronic acid was used instead of (9,9-diphenyl-9H-fluoren-2-yl)boronic acid (MS:[M+H]$^+$=546).

The compound 11 (cpd 11) was prepared in the same manner as in Synthesis Example 1, except that a compound 11-B (cpd 11-B) was used instead of a compound 1-B (cpd 1-B), and (4'-cyano-[1,1'-biphenyl]-4-yl)boronic acid was used instead of (4-cyanophenyl)boronic acid (MS:[M+H]$^+$=689).

Synthesis Example 8: Synthesis of Heterocyclic Compound

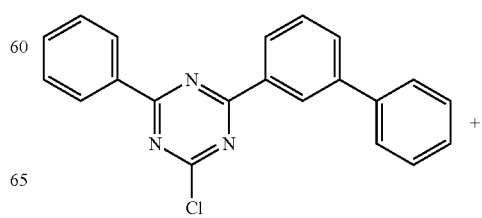

-continued

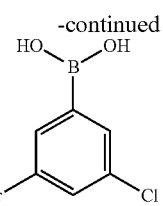

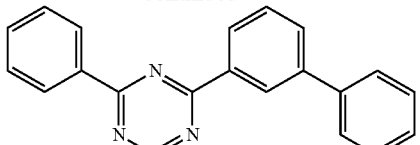

cpd 12

The compound 12-A (cpd 12-A) was prepared in the same manner as in Synthesis Example 1, except that 2-([1,1'-biphenyl]-3-yl)-4-chloro-6-phenyl-1,3,5-triazine was used instead of 2-chloro-4,6-diphenyl-1,3,5-triazine (MS:[M+H]$^+$=498).

The compound 12-B (cpd 12-B) was prepared in the same manner as in Synthesis Example 1, except that a compound 12-A (cpd 12-A) was used instead of a compound 1-A (cpd 1-A), and naphthalene-2-ylboronic acid was used instead of (9,9-diphenyl-9H-fluoren-2-yl)boronic acid (MS:[M+H]$^+$=546).

The compound 12 (cpd 12) was prepared in the same manner as in Synthesis Example 1, except that a compound 12-B (cpd 12-B) was used instead of a compound 1-B (cpd 1-B), and (4'-cyano-[1,1'-biphenyl]-4-yl)boronic acid was used instead of (4-cyanophenyl)boronic acid (MS:[M+H]$^+$=689).

Synthesis Example 9: Synthesis of Heterocyclic Compound

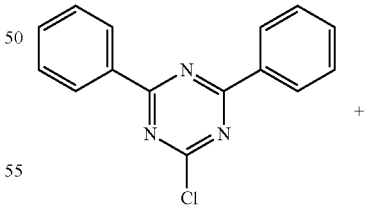

cpd 12-A

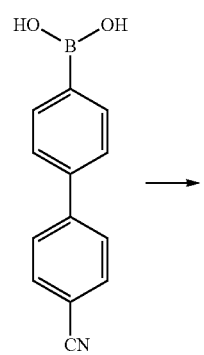

cpd 12-B

32
Synthesis Example 10: Synthesis of Heterocyclic Compound
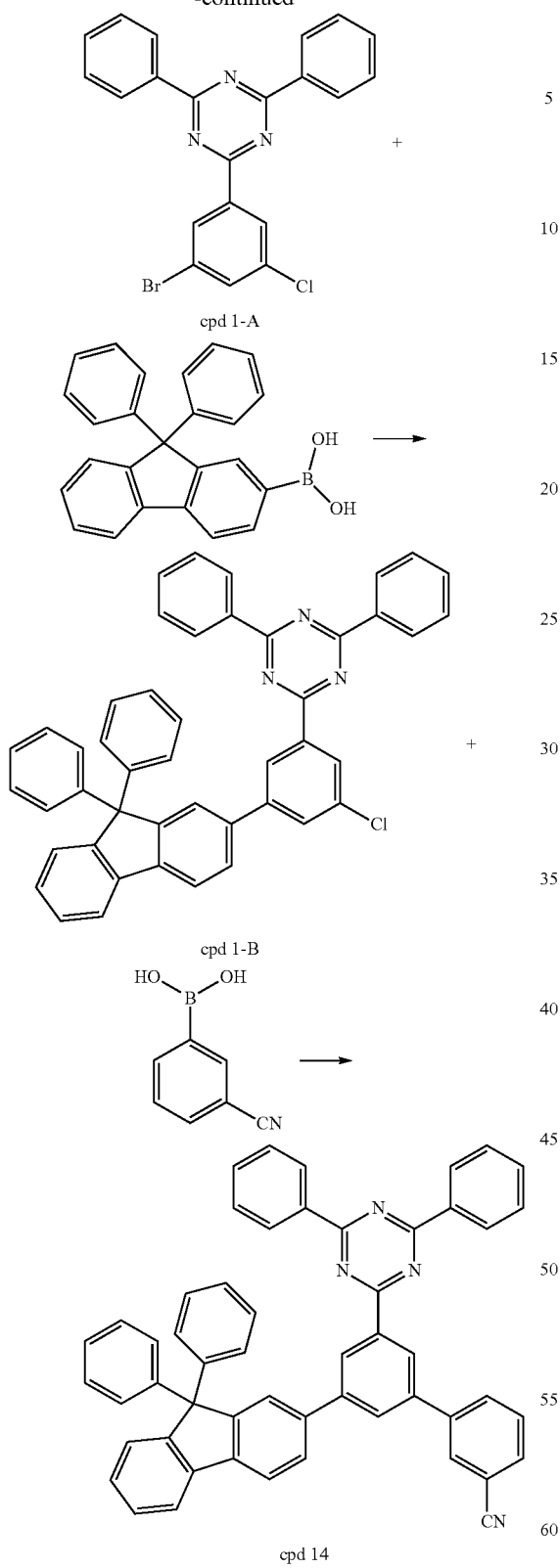
cpd 1-A
cpd 1-B
cpd 14
The compound 14 (cpd 14) was prepared in the same manner as in Synthesis Example 1, except that (3-cyanophenyl)boronic acid was used instead of (4-cyanophenyl)boronic acid (MS:[M+H]$^+$=727).
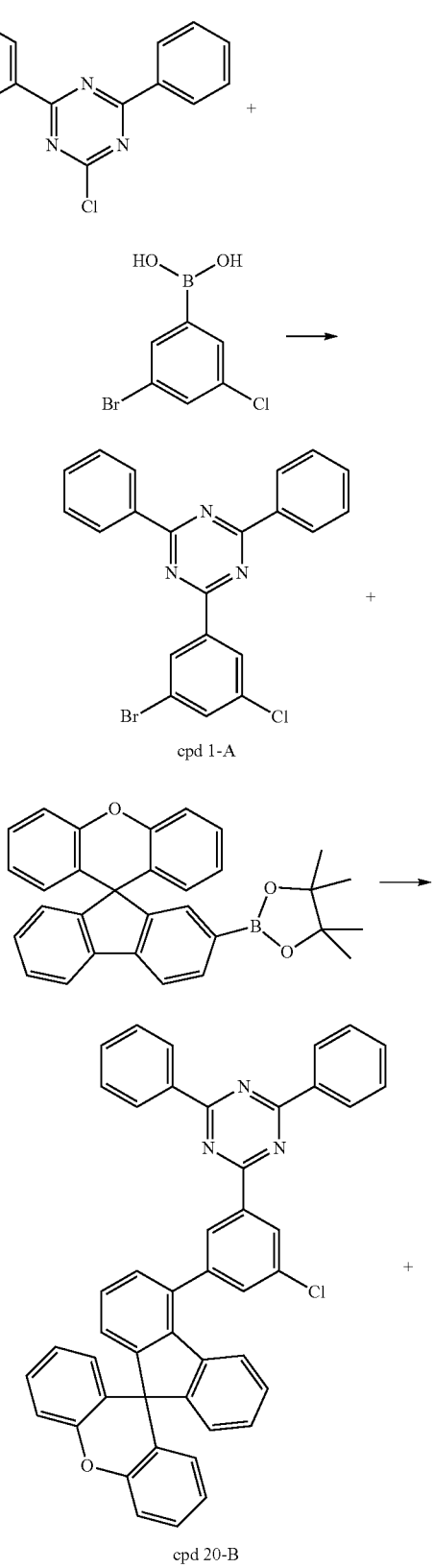
cpd 1-A
cpd 20-B -continued

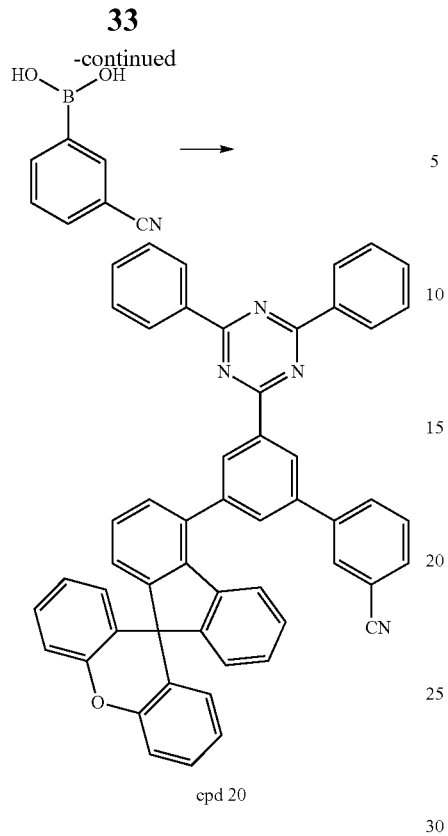

cpd 20

The compound 20-B (cpd 20-B) was prepared in the same manner as in Synthesis Example 1, except that 4,4,5,5-tetramethyl-2-(spiro[fluorene-9,9'-xanthen]-4-yl)-1,3,2-dioxaborolane was used instead of (9,9-diphenyl-9H-fluoren-2-yl)boronic acid (MS:[M+H]$^+$=674).

The compound 20 (cpd 20) was prepared in the same manner as in Synthesis Example 9, except that a compound 20-B (cpd 20-B) was used instead of a compound 1-B (cpd 1-B)(MS:[M+H]$^+$=741).

Example 1: Preparation of Organic Light Emitting Device

A glass substrate on which ITO (indium tin oxide) was coated to a thickness of 1000 Å was put into distilled water in which a detergent was dissolved, and ultrasonically washed. In this case, a product manufactured by Fischer Co., was used as the detergent, and distilled water filtered twice using a filter manufactured by Millipore Co. was used as the distilled water. After the ITO substrate was washed for 30 minutes, then ultrasonic washing was conducted twice using distilled water for 10 minutes. After the washing using distilled water was completed, ultrasonic washing was conducted using solvents of isopropyl alcohol, acetone, and methanol for 10 minutes, and then dried, after which it was transferred to a plasma cleaner. In addition, the substrate was cleaned for 5 minutes using oxygen plasma, and then transferred to a vacuum depositor.

On the ITO electrode thus prepared, the following Compound [HI-A] was thermally vacuum-deposited to a thickness of 600 Å to form a hole injection layer. The following hexanitrile hexaazatriphenylene (HAT) (50 Å) and the following compound [HT-A] (600 Å) were sequentially vacuum-deposited on the hole injection layer to form a hole transport layer.

The following compounds [BH] and [BD] were vacuum-deposited at a weight ratio of 25:1 on the hole transport layer to form a light emitting layer with a thickness of 200 Å. The compound 1 (cpd 1) and the following compound [LiQ (lithium quinolate)] were vacuum-deposited at a weight ratio of 1:1 on the light emitting layer to form an electron injection and transport layer with a thickness of 350 Å. Lithium fluoride (LiF) in a thickness of 10 Å and aluminum in a thickness of 1000 Å were sequentially deposited on the electron injection and transport layer to form a cathode In the above process, the vapor deposition rate of the organic material was maintained at 0.4 to 0.9 Å/s, the vapor deposition rate of lithium fluoride of the cathode was maintained at 0.3 Å/s, the vapor deposition rate of aluminum was maintained at 2 Å/s, and the degree of vacuum during vapor deposition was maintained at $1\times10^{-7}\sim5\times10^{-8}$ torr, thereby manufacturing an organic light emitting device.

[HAT]

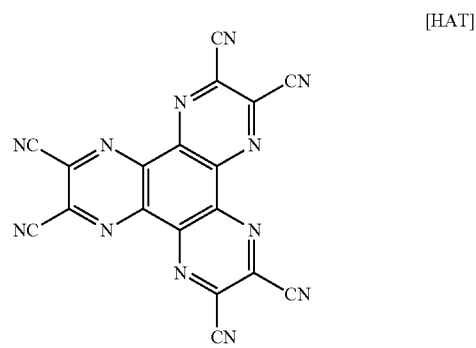

[HI-A]

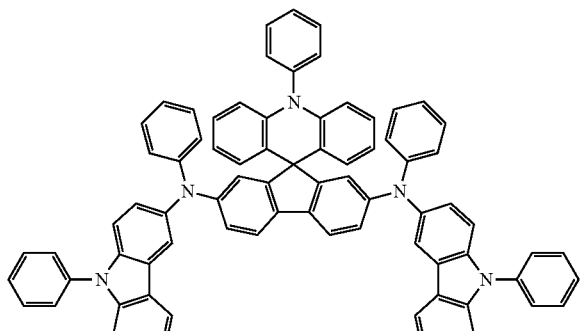

[HT-A]

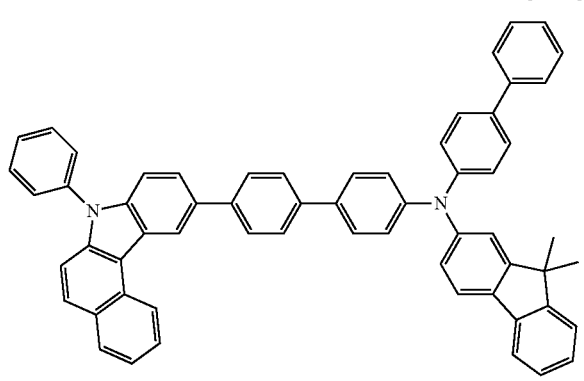

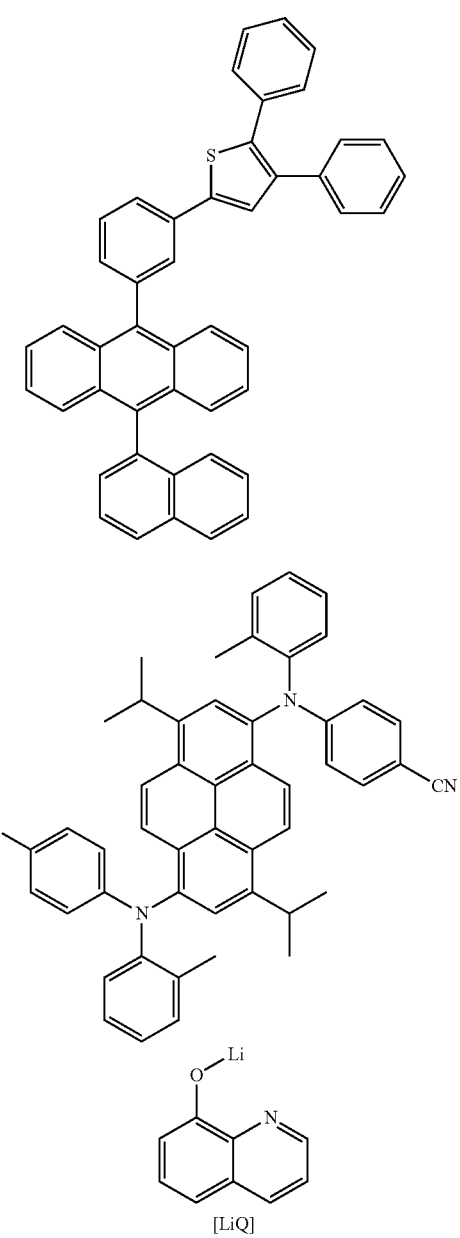

[BH]

[BD]

[LiQ]

Example 2: Preparation of Organic Light Emitting Device

An organic light emitting device was manufactured in the same manner as in Example 1, except that the compound 2 (cpd 2) was used instead of the compound 1 (cpd 1) in Example 1 to form an electron injection and transport layer.

Example 3: Preparation of Organic Light Emitting Device

An organic light emitting device was manufactured in the same manner as in Example 1, except that the compound 5 (cpd 5) was used instead of the compound 1 (cpd 1) in Example 1 to form an electron injection and transport layer.

Example 4: Preparation of Organic Light Emitting Device

An organic light emitting device was manufactured in the same manner as in Example 1, except that the compound 6 (cpd 6) was used instead of the compound 1 (cpd 1) in Example 1 to form an electron injection and transport layer.

Example 5: Preparation of Organic Light Emitting Device

An organic light emitting device was manufactured in the same manner as in Example 1, except that the compound 8 (cpd 8) was used instead of the compound 1 (cpd 1) in Example 1 to form an electron injection and transport layer.

Example 6: Preparation of Organic Light Emitting Device

An organic light emitting device was manufactured in the same manner as in Example 1, except that the compound 9 (cpd 9) was used instead of the compound 1 (cpd 1) in Example 1 to form an electron injection and transport layer.

Example 7: Preparation of Organic Light Emitting Device

An organic light emitting device was manufactured in the same manner as in Example 1, except that the compound 11 (cpd 11) was used instead of the compound 1 (cpd 1) in Example 1 to form an electron injection and transport layer.

Example 8: Preparation of Organic Light Emitting Device

An organic light emitting device was manufactured in the same manner as in Example 1, except that the compound 12 (cpd 12) was used instead of the compound 1 (cpd 1) in Example 1 to form an electron injection and transport layer.

Example 9: Preparation of Organic Light Emitting Device

An organic light emitting device was manufactured in the same manner as in Example 1, except that the compound 14 (cpd 14) was used instead of the compound 1 (cpd 1) in Example 1 to form an electron injection and transport layer.

Example 10: Preparation of Organic Light Emitting Device

An organic light emitting device was manufactured in the same manner as in Example 1, except that the compound 20 (cpd 20) was used instead of the compound 1 (cpd 1) in Example 1 to form an electron injection and transport layer.

Comparative Example 1: Preparation of Organic Light Emitting Device

An organic light emitting device was manufactured in the same manner as in Example 1, except that the following compound ET1 was used instead of the compound 1 (cpd 1) in Example 1 to form an electron injection and transport layer.

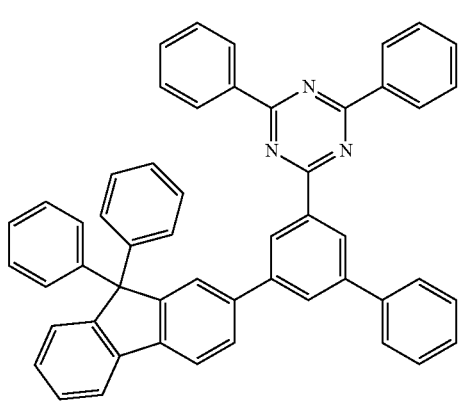

[ET1]

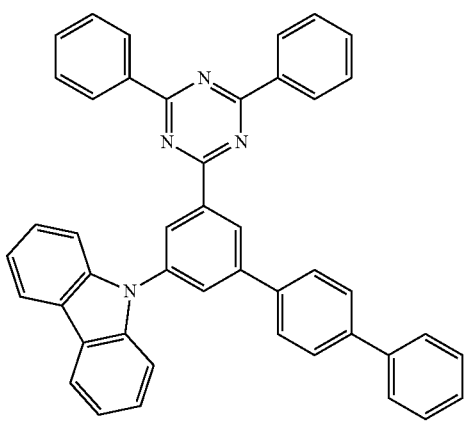

[ET3]

Comparative Example 2: Preparation of Organic Light Emitting Device

An organic light emitting device was manufactured in the same manner as in Example 1, except that the following compound ET2 was used instead of the compound 1 (cpd 1) in Example 1 to form an electron injection and transport layer.

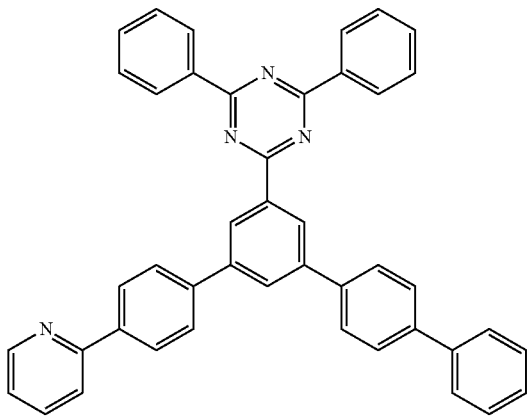

[ET2]

Comparative Example 3: Preparation of Organic Light Emitting Device

An organic light emitting device was manufactured in the same manner as in Example 1, except that the following compound ET3 was used instead of the compound 1 (cpd 1) in Example 1 to form an electron injection and transport layer.

Comparative Example 4: Preparation of Organic Light Emitting Device

An organic light emitting device was manufactured in the same manner as in Example 1, except that the following compound ET4 was used instead of the compound 1 (cpd 1) in Example 1 to form an electron injection and transport layer.

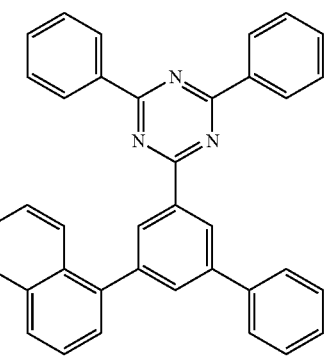

[ET4]

Test Example: Evaluation of Performance of Organic Light Emitting Device

The driving voltage and luminous efficiency of the organic light emitting devices manufactured in accordance with Examples 1 to 10 and Comparative Examples 1 to 4 were measured at a current density of 10 mA/cm². The lifetime (T90), which is defined as the time required for the luminance to decrease to 90% of its initial value, was measured at a current density of 20 mA/cm². The measurement results are shown in Table 1 below.

TABLE 1

| | Compound | Driving voltage (V) | Current efficiency (cd/A) | Color coordinates (x, y) | Lifetime (LT90 at 20 mA/cm²) |
|---|---|---|---|---|---|
| Example 1 | 1 | 3.78 | 5.19 | (0.142, 0.097) | 117 |
| Example 2 | 2 | 3.63 | 5.30 | (0.142, 0.097) | 109 |

TABLE 1-continued

| Com-pound | Driving voltage (V) | Current efficiency (cd/A) | Color coordinates (x, y) | Lifetime (LT90 at 20 mA/cm$^2$) |
|---|---|---|---|---|
| Example 3 | 5 | 3.81 | 5.29 | (0.142, 0.096) | 136 |
| Example 4 | 6 | 3.72 | 5.24 | (0.142, 0.097) | 115 |
| Example 5 | 8 | 3.79 | 5.16 | (0.142, 0.096) | 120 |
| Example 6 | 9 | 3.68 | 5.21 | (0.142, 0.097) | 121 |
| Example 7 | 11 | 3.76 | 5.15 | (0.142, 0.096) | 135 |
| Example 8 | 12 | 3.75 | 5.23 | (0.142, 0.096) | 119 |
| Example 9 | 14 | 3.80 | 5.12 | (0.142, 0.096) | 123 |
| Example 10 | 20 | 3.68 | 5.28 | (0.142, 0.096) | 109 |
| Comparative Example 1 | ET1 | 4.82 | 3.93 | (0.142, 0.098) | 82 |
| Comparative Example 2 | ET2 | 4.89 | 4.21 | (0.142, 0.096) | 88 |
| Comparative Example 3 | ET3 | 5.08 | 4.18 | (0.142, 0.096) | 91 |
| Comparative Example 4 | ET4 | 4.79 | 3.87 | (0.142, 0.096) | 79 |

From the results shown in Table 1, it is confirmed that the compound represented by Chemical Formula 1 according to one embodiment of the present disclosure can be used for an organic material layer capable of performing electron injection and electron transport of an organic light emitting device at the same time.

Specifically, it is confirmed that the organic light emitting devices of Examples 1 to 10 exhibit a low driving voltage, high luminous efficiency, and a long lifetime by using the compounds represented by Chemical Formula 1, that is, the compounds in which both substituents (Ar$^3$ and Ar$^4$) of the phenyl group connected to triazine differ from each other, either one substituent (Ar$^3$) of the both substituents is an aryl group or a heteroaryl group having 10 or more carbon atoms, and another substituent (Ar$^4$) is an aryl group substituted with a cyano group.

On the other hand, in Comparative Examples 1 to 4, the compounds in which both substituents of the phenyl group connected to triazine differ from each other, but either one of the two substituents is not an aryl group substituted with a cyano group is used as the material of the electron injection and transport layer. Specifically, in Comparative Examples 1 and 4, a compound in which Ar$^4$ in Formula 1 is a phenyl group is used, in Comparative Example 2, a compound in which Ar$^4$ in Formula 1 is a pyridylphenyl group is used, and in Comparative Example 3, a compound in which Ar$^4$ in Formula 1 is a carbazolyl group is used.

Comparing Examples 1 to 10 with Comparative Examples 1 to 4, it is confirmed that Examples 1 to 10 using the compound represented by Chemical Formula 1 exhibit a lower driving voltage, higher luminous efficiency, and a longer lifetime than those of the comparative examples.

EXPLANATION OF SIGNS

1: substrate
2: anode
3: light emitting layer
4: cathode
5: hole injection layer
6: hole transport layer
7: light emitting layer
8: electron transport layer

The invention claimed is:

1. A compound represented by the following Chemical Formula 1:

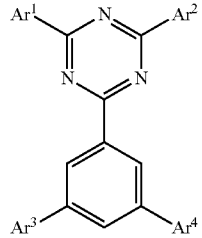

[Chemical Formula 1]

wherein, in Chemical Formula 1,

Ar$^1$ and Ar$^2$ are each independently a substituted or unsubstituted aryl group having 6 to 60 carbon atoms, Ar$^3$ is a monovalent group derived from an arene selected from the group consisting of naphthalene, biphenyl, terphenyl, triphenylene, phenanthrene, phenyl naphthalene, 9,9-dimethylfluorene, 9,9-diphenylfluorene, and spiro[fluorene-9,9'-fluorene], or a monovalent group derived from a heteroarene selected from the group consisting of spiro[fluorene-9,9'-xanthenel] and spiro[fluorene-9,9'-thioxanthenel], and Ar$^4$ is a monovalent group derived from an arene selected from the group consisting of benzene, naphthalene, biphenyl, terphenyl, triphenylene, phenanthrene, phenyl naphthalene, 9,9-dimethylfluorene, 9,9-diphenylfluorene, and spiro[fluorene-9,9'-fluorene], and substituted with a cyano group.

2. The compound of claim 1, wherein Ar$^1$ and Ar$^2$ are each independently a phenyl group or a biphenyl group.

3. The compound of claim 1, wherein Ar$^4$ is a substituent selected from the group consisting of the following substituent groups:

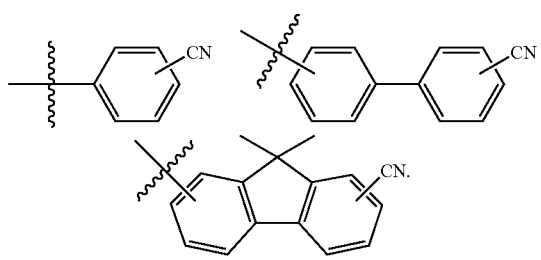

4. The compound of claim 1, wherein the compound represented by Chemical Formula 1 is a compound selected from the group consisting of compounds represented by the following Chemical Formulae 1-1 and 1-2:

[Chemical Formula 1-1]

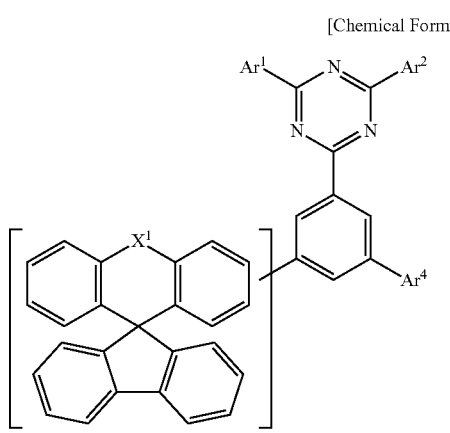

wherein, in Chemical Formula 1-1, $X^1$ is a non-bond, a single bond, O, or S, and $Ar^1$, $Ar^2$, and $Ar^4$ are the same as defined in Chemical Formula 1,

[Chemical Formula 1-2]

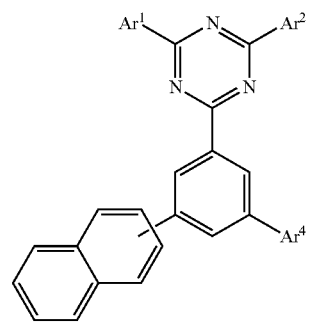

wherein, in Chemical Formula 1-2, $Ar^1$, $Ar^2$, and $Ar^4$ are the same as defined in Chemical Formula 1.

5. The compound of claim 1, wherein the compound is selected from the group consisting of the following compounds:

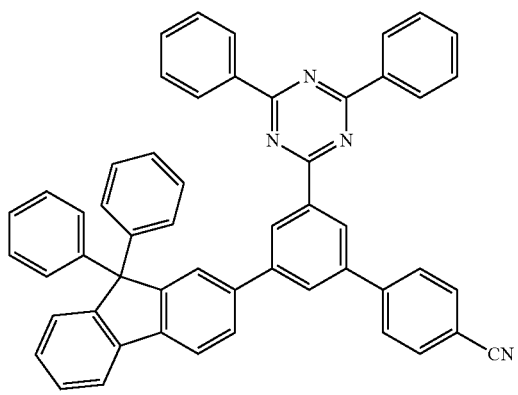

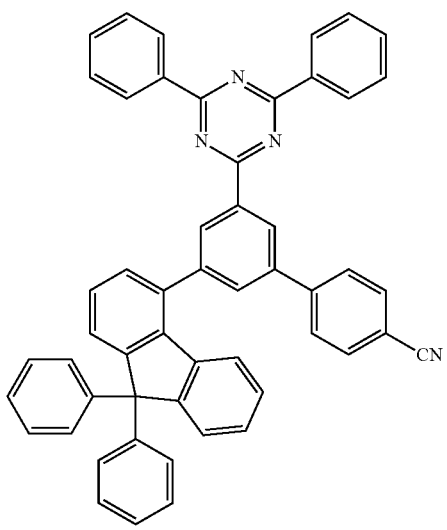

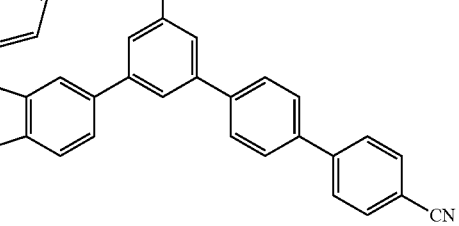

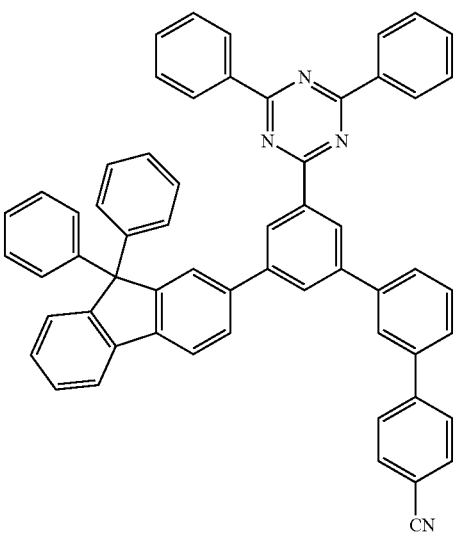

-continued
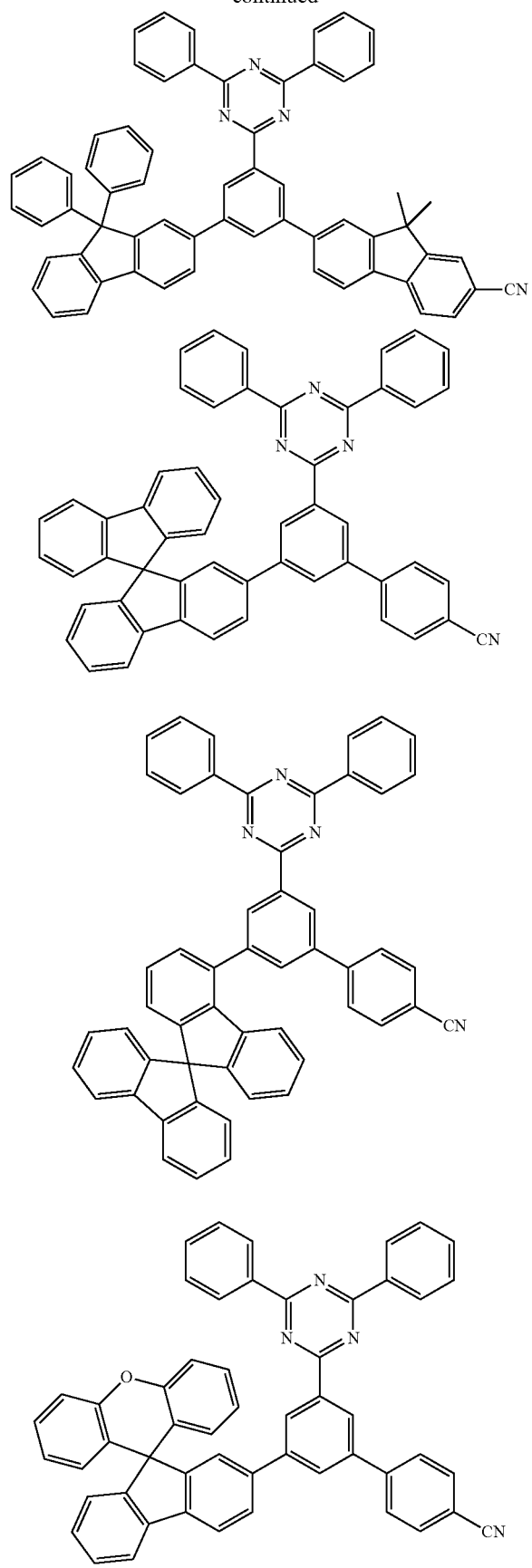
-continued
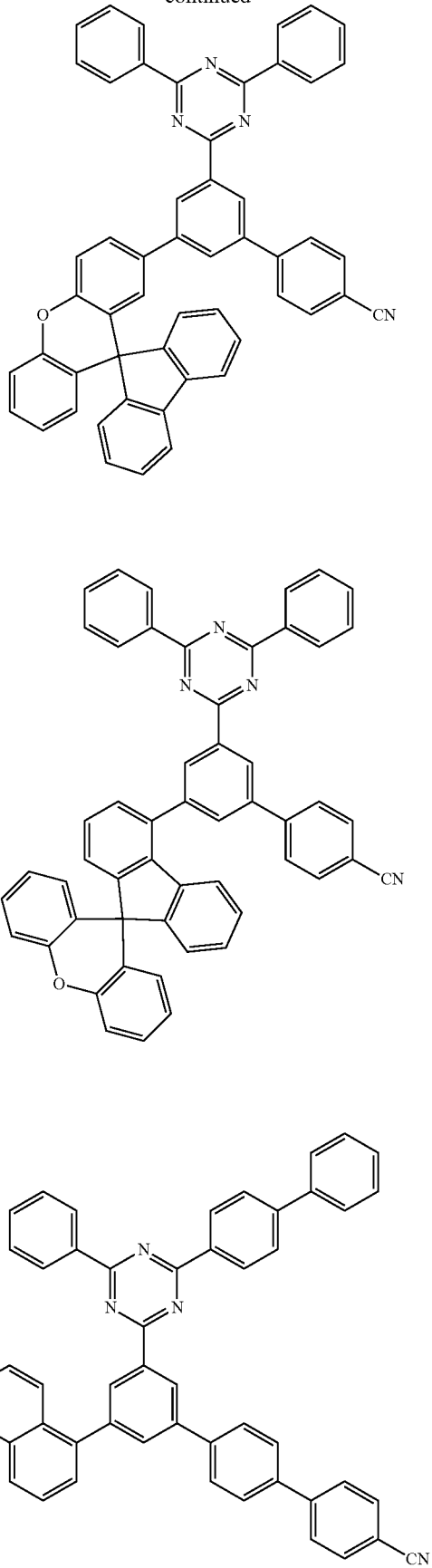

45
-continued
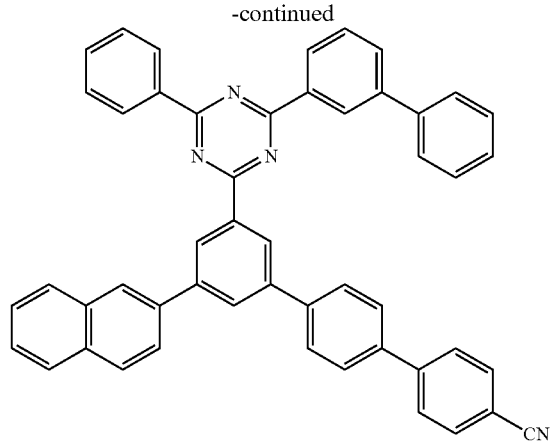
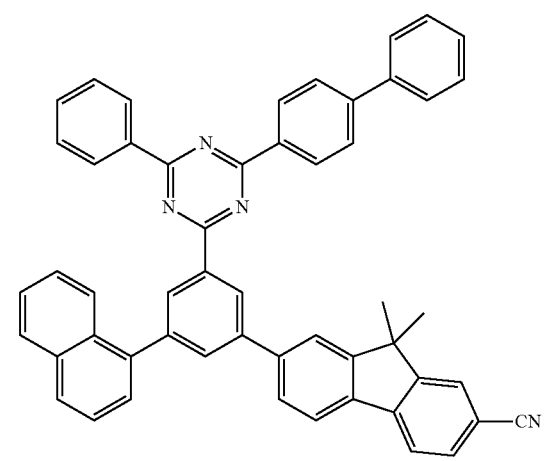
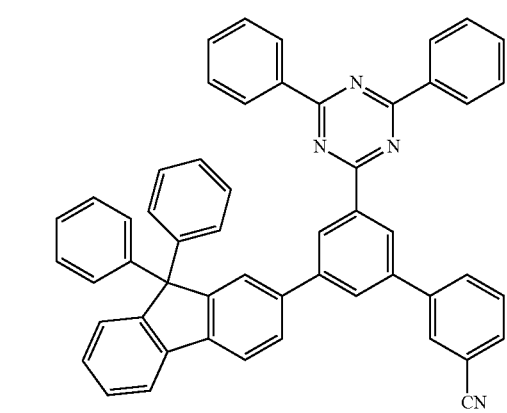
46
-continued
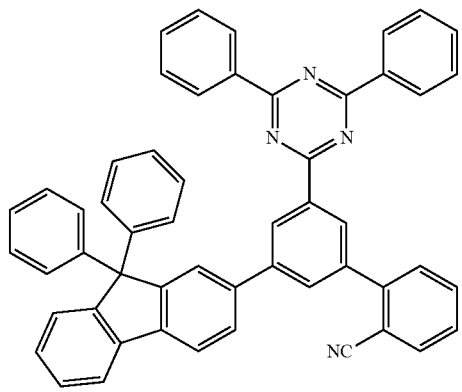
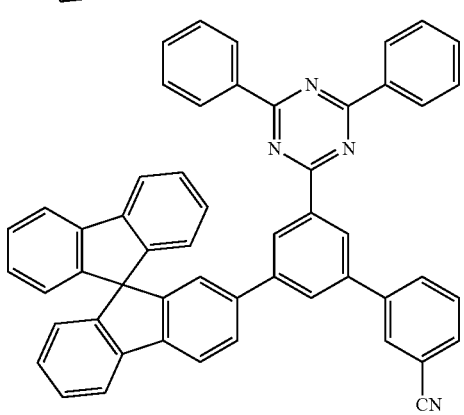
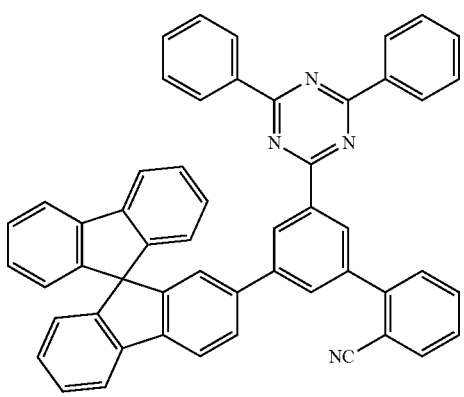
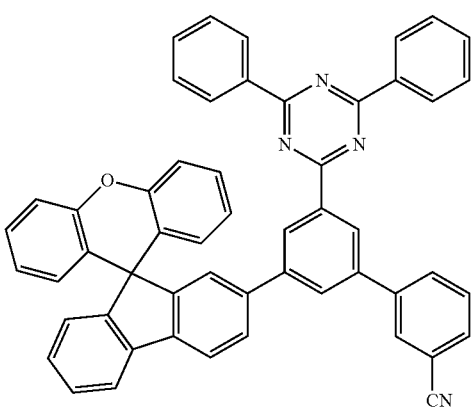

-continued
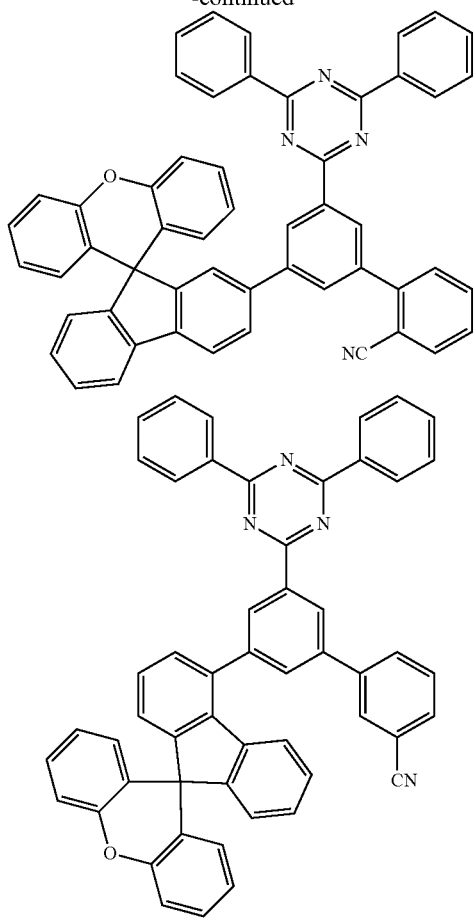
-continued
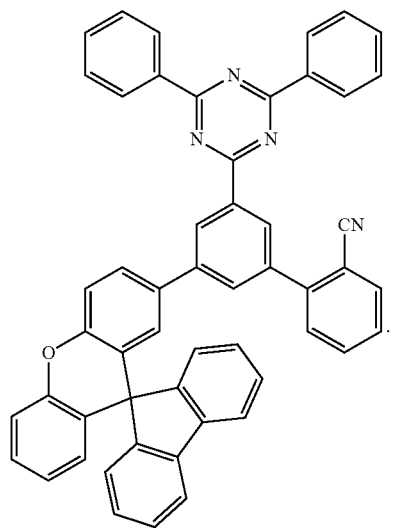
6. An organic light emitting device comprising: a first electrode; a second electrode facing the first electrode; and at least one layer of the organic material layers provided between the first electrode and the second electrode, wherein the at least one layer of the organic material layers include the compound of claim 1.
* * * * *